(12) United States Patent
Gislason et al.

(10) Patent No.: US 9,078,949 B2
(45) Date of Patent: Jul. 14, 2015

(54) COMPOSITIONS OF PARTIALLY DEACETYLATED CHITIN DERIVATIVES

(75) Inventors: Johannes Gislason, Mosfellsbae (IS); Jon M. Einarsson, Reykjavik (IS); Ng Chuen How, Reykjavik (IS); Sven Bahrke, Wandlitz (DE)

(73) Assignee: GENIS HF., Siglufjordur (IS)

( * ) Notice: Subject to any disclaimer, the term of this patent is extended or adjusted under 35 U.S.C. 154(b) by 1538 days.

(21) Appl. No.: 11/922,014

(22) PCT Filed: Jun. 14, 2006

(86) PCT No.: PCT/IS2006/000013
§ 371 (c)(1),
(2), (4) Date: Mar. 6, 2008

(87) PCT Pub. No.: WO2006/134614
PCT Pub. Date: Dec. 21, 2006

(65) Prior Publication Data
US 2009/0281058 A1   Nov. 12, 2009

(30) Foreign Application Priority Data
Jun. 14, 2005 (IS) .............................................. 7895

(51) Int. Cl.
| | | |
|---|---|---|
| *A61K 31/722* | (2006.01) | |
| *C08B 37/08* | (2006.01) | |
| *A61L 26/00* | (2006.01) | |
| *A61L 24/08* | (2006.01) | |
| *A61L 27/20* | (2006.01) | |

(52) U.S. Cl.
CPC ............. *A61L 26/0028* (2013.01); *A61L 24/08* (2013.01); *A61L 27/20* (2013.01); *C08B 37/003* (2013.01)

(58) Field of Classification Search
USPC ................................ 514/55, 54; 536/20, 55.3
See application file for complete search history.

(56) References Cited

U.S. PATENT DOCUMENTS

| | | | |
|---|---|---|---|
| 2,795,579 A | 6/1957 | Doczi | |
| 5,077,052 A | 12/1991 | Franzoni et al. | |
| 2002/0084194 A1* | 7/2002 | Redepenning | ................ 205/316 |
| 2003/0158302 A1* | 8/2003 | Chaput et al. | ................. 524/115 |
| 2005/0004073 A1 | 1/2005 | Gislason et al. | |

FOREIGN PATENT DOCUMENTS

| | | |
|---|---|---|
| CN | 1554267 A | 12/2004 |
| FR | 2 701 266 A | 8/1994 |
| JP | 2005023464 A * | 1/2005 |

OTHER PUBLICATIONS

Ikoma et al. ; JP 2005023464 A; Jan. 1, 2005 (English Translation (Machine)).*
Xiaogan College; CN 1554267 A; Dec. 15, 2004 (English Translation (Machine)).*

* cited by examiner

*Primary Examiner* — Shaojia Anna Jiang
*Assistant Examiner* — Michael C Henry
(74) *Attorney, Agent, or Firm* — Birch, Stewart, Kolasch & Birch, LLP.

(57) ABSTRACT

The present invention relates to compositions comprising biologically active chitinous oligomers and their endotoxin purified and partially deacetylated chitin polymer precursors, and their use in pharmaceutical compositions, biomaterial compositions, medical devices, and processes to produce the said oligomers. More specifically the present invention relates to novel compositions and processes to produce such compositions. The compositions include therapeutic hetero polymer and hetero oligomer compositions comprising specific sequences of N-acetyl glucosamine and glucosamine, developed to optimize chemical and structural features which are important for the therapeutic activity of these compositions. In addition, the present invention provides methods to use degree of deacetylation of a partially deacetylated chitin polymer in order to modulate physical and biological parameters in a calcium phosphate composite for bone implant applications.

4 Claims, 19 Drawing Sheets

Figure 1:
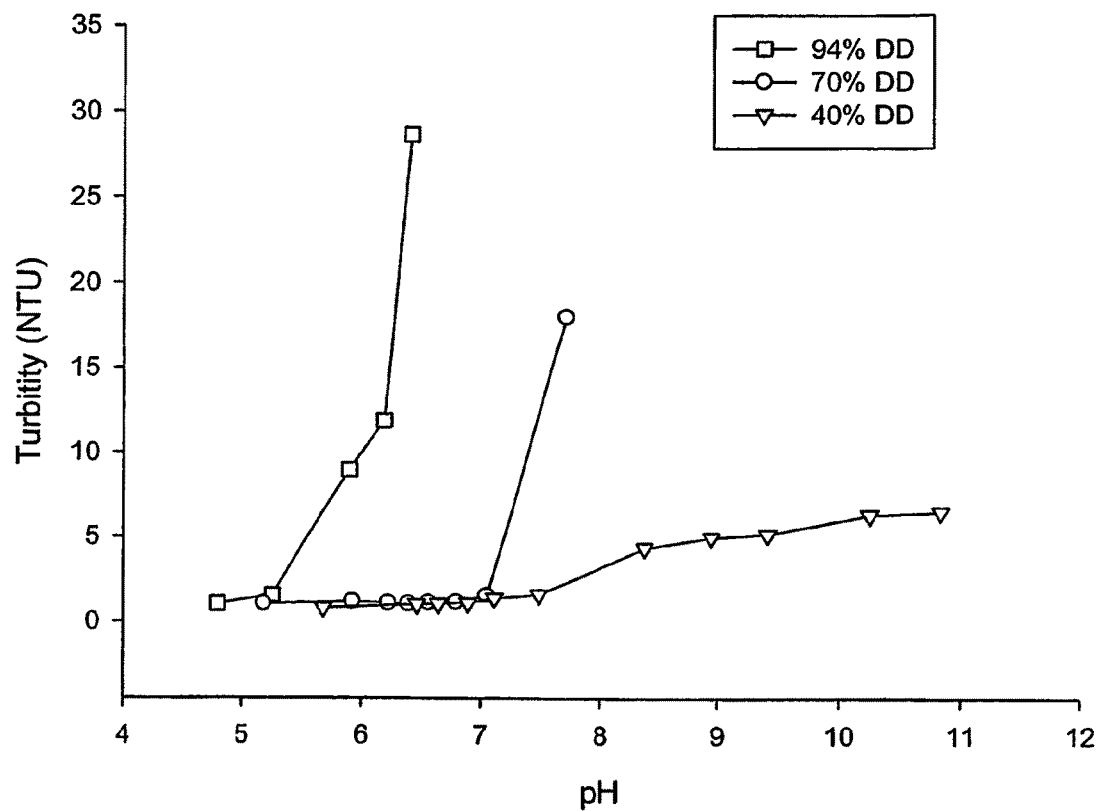

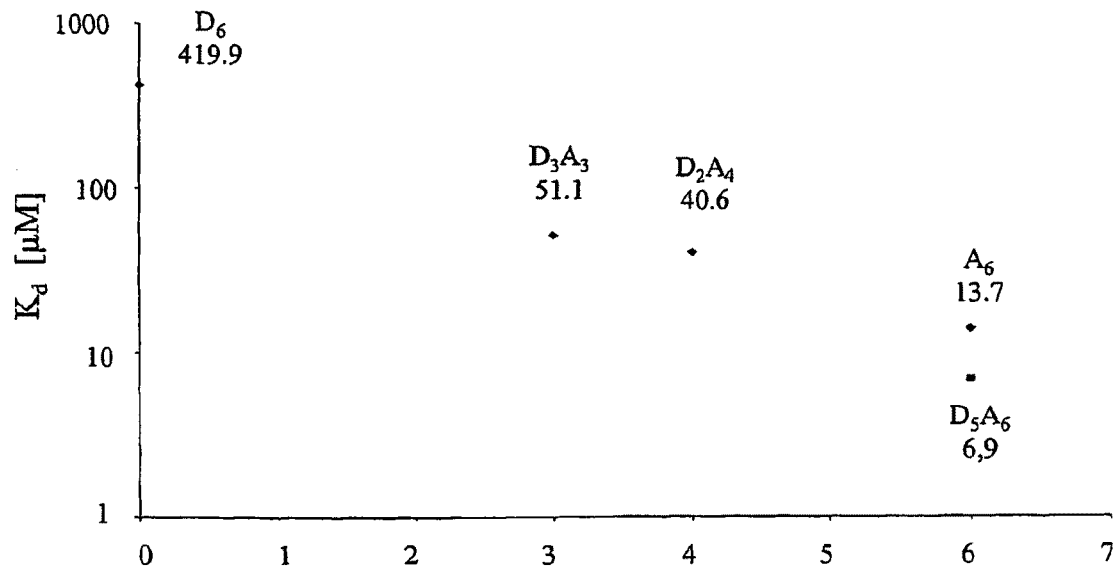
FIG. 16 — Number of N-acetyl groups
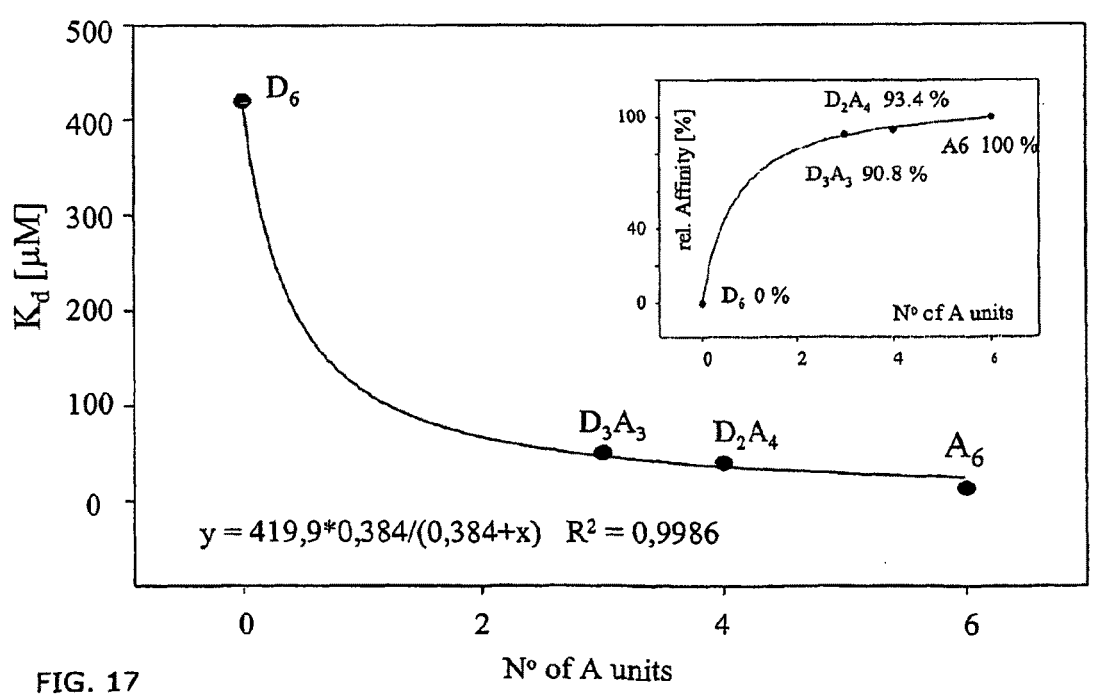
FIG. 17 — N° of A units

Bone resorption mean

COMPOSITIONS OF PARTIALLY DEACETYLATED CHITIN DERIVATIVES

FIELD OF INVENTION

The present invention relates to a novel method to recover polymeric chitosan from solution. The invention further relates to compositions produced by the method of the invention comprising biologically active chitinous polymers and oligomers and their use in pharmaceutical compositions, biomaterial compositions, medical devices, and processes to produce the said polymers and oligomers.

BACKGROUND OF THE INVENTION

Chitosan is a biopolymer of natural origin, derived from chitin which is obtainable from crustacean shell, but can also be obtained from other invertebrates and from fungi. Chitosan is prepared by deacetylation of the N-acetyl glucosamine residues of the chitin polymer, typically by hydrolyzing the N-acetyl linkages with concentrated alkali. By definition, chitosan is generally described as a copolymer of D-glucosamine (D) and N-acetyl-D-glucosamine (A), which is insoluble in water at pH above 6.2—the isoelectric point of the free amine group—but dissolves at pH below about 6.2. Typically, 70-100% of the monomeric units in conventional chitosan copolymer are D-glucosamine, which can be described as 70-100% deacetylated chitosan with a degree of deacetylation of 70-100%. When the degree of deacetylation is lower than about 70%, the chitosan polymer displays different solubility properties, increased bioactivity, and generally higher biodegradability.

Chemical and biological properties of chitosan are directly influenced by the degree of deacetylation (DD) and degree of polymerisation (DP), i.e. the chain length of the polymer. In solution at pH below 6.2, and when amine groups of the D-glucosamine residues are protonated, chitosan is a positively charged polymer. Being an amine, chitosan is a weak base and can form salts with acids, such as carboxylic and mineral acids. Most of these salts are water-soluble. In its natural form, chitin is insoluble in water. However, it can be made water-soluble by partial deacetylation through alkali treatment. Partially deacetylated chitin with DD of 35-50% is soluble in water at a wide range of pH. This form of partially deacetylated chitin has been shown to be bioactive with potential applications in various fields such as in biomedicine, pharmaceuticals, cosmetics, etc.

One of the drawbacks of chitosan preparations with more than 60-70% DD is its tendency to precipitate at pH above 6.2. This limits its spectrum of applications where solubility at neutral to high pH is require. In this respect, the partially deacetylated chitin has greater advantages over chitosan with higher DD, since its solubility profile covers a wider range of pH. It inherits most of the physical-chemical properties of chitosan and possesses higher water holding capacity as compared to normal chitosan. resulting in rapid swelling when in contact with water and posses balanced hydrophilic/hydrophobic properties as compared to regular higher DD chitosan. These properties represent an immense potential in various applications in biomedical, pharmaceutical, cosmetic and other related industries.

Biological activity of chitin and chitosan is abundantly documented in the literature, and growing evidences indicate that bioactivity is increased with lower DD. This goes hand in hand with improved solubility properties at physiological pH.

Purification of chitosan commonly involves a dissolution process so as to remove insolubles or impurities from the solution. This is followed by recovery process through precipitation of chitosan from the solution. The recovery of chitosan in a form of precipitate, can then be washed to neutral pH and to remove salt. This recovery is generally not a problem for chitosan with 55% DD and above, since it can be precipitated easily by increase the solution pH to above 6.2. However, adjustment of pH is not effective for partially deacetylated chitin, usually an organic solvent is needed to aid the precipitation process. Patent No. CN1554267 reported the use of ethanol for washing the polymer and more examples on the use of solvents can be found in patents JP10072502, CN1371922, etc. Alternatively, in a less adequate method, the solution is just filtered and dried, whereby salt will be present in the product (JP2022301).

Chitosan has been shown to be biocompatible and biodegradable, making it an attractive choice as an ingredient in biomaterials for bioengineering applications. Biomaterials are generally defined as synthetic materials used to replace part of a living system or to function in intimate contact with living tissue, and chitosan has generally been considered as a suitable inert component in biomaterial formulations or as a matrix for other substances or ingredients. Chitosan has been suggested as a drug delivery carrier as it can immobilize a large amount of bioactive substances through adsorption or by covalently binding such substances through simple chemical reactions.

WO 2004/028578 discloses a composition for bone formation and bone consolidation in bone extension comprising chitosan, tripolyphosphate and bone morphogenic protein (BMP). Further, US 2003/0124172 discloses a method for producing chitosan-based films comprising a biodegradable polymer and BMP for enhancing osteointegration of dental implants or in traumatic situations.

Bioactivity of chitin-derived materials has been indicated, e.g. in EP 1435976 that discloses chitooligomer compositions comprising heterooligomers of N-acetyl-glucosamine and glucosamine, which are biologically active and are suggested as active ingredients in medicaments for treating conditions in connective tissue, in particular arthritis and osteoarthritis.

In an other patent application it is suggested that chitinase like proteins (CLPs) expressed by the genomes of humans and other vertebrates, represent target receptors involved in the bioactivity of these chitooligomers, inducing a signalling response when binding to the chitooligomers. These chitinase like proteins derive from a family of genes expressing the Family 18 Chitinases in most forms of living organisms. The active side of the Family 18 Chitinases is well preserved in the CLPs, with the exception that most of these proteins have lost their catalytic activity through key mutations in the active side. However, in humans, at least two of these proteins maintain their chitinolytic activity i.e. Acetic Mammalian Chitinase (AMCase) and Chitotriosidase.

SUMMARY OF THE INVENTION

It is an object of the present invention to provide methods and compositions of highly purified partially deacetylated chitin for therapeutic applications. Upon extensive hydrolysis with a Family 18 Chitinase, either in vitro or in vivo, the partially deacetylated polymeric composition will generate chitinous hetero polysaccharides with therapeutic activity. Hence the invention provides two forms of compositions; polymeric compositions substantially purified from organic contaminants such as bacterial endotoxins, suitable as active ingredients into biomaterials for implant applications, and oligomeric compositions suitable for systemic administration. These polymeric and oligomeric compositions, herein referred to as "Chitobiomers", comprise biologically relevant features which are distinctively different from conventional chitosan and prior art chitin derived materials. Furthermore, the oligomeric compositions provided by current invention represent optimization of the therapeutic activity of the entire Chitobiomer compositions including; bioavailability, biostability, and bioactivity. These oligomeric compositions are herein referred to as "Therapeutic Chitooligosaccharides" (T-ChOS). The polymeric compositions provide an excellent in situ delivery system whereby endogenous Family 18 chitinases, specifically expressed by local macrophages, gradually degrade the polymeric substrate in situ, generating therapeutically active T-ChOS capable of preventing scar tissue formation and inducing tissue regeneration in injured cartilage and bone tissues. This involves reduction or inhibition of fibroblast activity in the injured tissue by the T-ChOS compositions, parallel to an activation of tissue specific cartilage and bone progenitor cells. The oligomeric compositions however, can also be produced in vitro on a commercial bases by extensive hydrolyses of the polymeric Chitobiomer compositions by a Family 18 Chitinase, providing T-ChOS for any kind of systemic delivery, such as oral, intramuscular, subcutaneous or intravenous administration, or local delivery in an implant composition.

In a first aspect of the present invention, an optimization of the process to produce partially deacetylated chitin hetero polymer (Chitobiomers) of therapeutic activity is provided. The optimization includes method for purifying a fully dissolved partially deacetylated chitin polymer, where the method comprises the steps of a) neutralizing the partially deacetylated chitin after deacetylation; b) dissolving the partially deacetylated chitin in acidic solution; c) removing undissolved particles through sequential filtering steps; d) adjusting the solution to pH above 8; and e) precipitating the dissolved partially deacetylated chitin increasing the chaotropic factor of the solution through elevated temperature and addition of salt. The method is characterized by the recovery of the precipitate after precipitation through sieving or by centrifugation and wherein the temperature of the precipitate is above 50° C. This optimization is particularly obtained through focusing on the hydrolysis products generated by extensive hydrolysis of the polymeric Chitobiomers by a Family 18 Chitinase. The substrate will be degraded into hetero-oligomers possessing substantial resistance to all Family 18 Chitinases. By carefully controlling the deacetylation step in the provided process, both in terms of homogeneity and degree of the deacetylation, the relative yield of T-ChOS compositions generated during the hydrolysis step can be controlled. This provides an optimization of the therapeutic activity of the Chitobiomer compositions. The defined polymeric Chitobiomer compositions are confined within the range of 30-70% degree of deacetylation, showing solubility properties substantially different from conventional chitosan. Due to this definition, all Chitobiomer composition exhibit solubility at physiological pH.

In a second aspect of the present invention a partially deacetylated chitin polymer composition is provided, which is produced according to the method of the invention. In an embodiment of this invention the composition comprising biologically active chitooligomers of N-acetyl glucosamine (A) and glucosamine (D). The composition of the chitooligomers has to fulfill all the following criteria (a-d):
a) said oligomers having a chain length in the range of 5-20 monomer residues
b) each oligomer chain can have two N-acetyl glucosamine residues (AA) on either or both ends of the oligomer chain,
c) the remaining internal part of the oligomer having a maximum amount of A residues
d) the sequence of said internal chain being such that an N-acetyl glucosamine residue (A) is not adjacent to another N-acetyl glucosamine residue (such as AA).

In a third aspect of the present invention a use of the compositions of the invention is provided for the manufacture of a biomaterial/medicament.

In a forth aspect of the present invention a pharmaceutical composition comprising oligomeric compositions of the Chitobiomer produced by the methods of the invention is provided.

In further aspect of the present invention the polymeric compositions of the Chitobiomers are used to modulate water activity in a calcium phosphate composite. The polymeric compositions of the Chitobiomers will limit the sizes of crystals formed during the setting and hardening of the composite, and together with degradation of the Chitobiomers by Family 18 Chitinase, expressed locally by macrophages; this enhances the bio-degradability of the composite and helps migratory cells to penetrate the scaffold, increasing its osteoconductivity.

DETAILED DESCRIPTION OF THE INVENTION

The embodiments and definitions below relate to the methods and the compositions and uses of the present invention.

In an embodiment of the present invention the degree of deacetylation (DD) of the partially deacetylated chitin polymer is between 25 to 70%, such as between 30 and 65%, such as between 30 to 60%, such as between 30 to 55%, where the DD is referring to the average DD of the soluble fraction of the partially deacetylated chitin and the molecular weight of this Chitobiomer is higher than about 10 kDa.

In the present context the term "neutralization" with respect to the partially deacetylated chitin mixture after deacetylation, refers to reducing the pH of a strong alkali solution in the process of deacetylation either by washing with water or by adding strong acid.

In an embodiment of the present invention the heating of the partially deacetylated chitin solution comprises raising the temperature to between 45-100° C. or even boiling, such as 55-90° C., or such as 60-80° C. or preferably between 60 and 70° C.

In an embodiment of the present invention the adjustment of the partially deacetylated chitin solution comprises raising the pH to between pH 8-13, such as between pH 9-12 or between 10-11.

In an embodiment of the present invention the salt precipitation is obtained through an addition of salt or through neutralization of the dissolved acid in the solution, wherein the salt used for the salt precipitation is sodium chloride or a salt of any organic acid used to dissolve the partially deacetylated chitin such as acetic add, or preferable dl or tricarboxylic acids such as malic acid or citric acid. These salts can be formed by neutralization of the solution with a suitable base. Furthermore, the salt concentration refers to any concentration that may lead to a precipitation of the polymer, where the salt concentration is between 2% and saturation.

In an embodiment of the present invention chitin is treated with mineral acid prior to the deacetylation step to obtain a product with very low endotoxin levels, such as between 1 and 60 EU/g or below 30 EU/g. The add opens up the polymer, exposes and destroys the endotoxins Any concentrated acid that leads to dissolution of the chitin polymer HCl, phosphoric, formic, nitric, sulfuric can be used. Endotoxin results are expressed as EU units as EU/ml, or EU/g.

In a further embodiment of the present invention the processes are used for the manufacture of a biomaterial/medicament for enhancing bone regeneration and hemostasis in the healing of a fractured or severed bone in a mammal. Such medicament enhances bone formation through endochondral ossification by activation of tissue specific progenitor cells.

In an embodiment of the present invention the biomaterial comprises a further component selected from the group consisting of calcium phosphates, including hydroxyapatite, calcium sulphate, sodium tripolyphosphate, alginate, collagen and hyaluronic acid.

Bioavailability, or the ability for a given substance to pas through biological membranes, is related to the hydrophobicity of the molecules. Since all biological membranes are predominantly of a hydrophobic nature, the general rule applies that the more hydrophobic a substance is the better it can penetrate such biological membranes. N-acetyl-glucosamine and fully acetylated chitin oligomers are more hydrophobic than the corresponding glucosamine monomer or highly deacetylated chitosan oligomers, suggesting that chitinous hetero oligomers will possess increased bioavailability with increased acetylation. Hence, the T-ChOS formulations have been optimized to contain a maximum amount of N-acetyl-glucosamine in their molecular structure in order to maximize their bioavailability, without jeopardizing their biostability. This invention provides unique data showing relatively increased bioavailability of the T-ChOS compositions in a human volunteer.

Biostability of an organic compound refers to its susceptibility to endogenous enzymes in a living organism and its half-life ($t\frac{1}{2}$) in that organism. The more susceptible the less biostable is the compound. In humans, chitinolytic enzymes can be divided into two groups; enzymes with high level chitinolytic specificity like Family 18 chitinases (AMCase, Chitotriosidase), possessing high specific activity, or enzymes with less chitinolytic specificity such as lysozyme and some proteases which happen to degrade chitin and chitosan but at lower specific activity. By partial deacetylation, the T-ChOS compositions have been optimized for maximum stability towards hydrolysis by Family 18 chitinase. Since these enzymes require a sequence of two or more consecutive N-acetyld-glucosamine residues as recognition for cleavage, the T-ChOS compositions are specifically optimized to exclude such sequences in the internal part of the molecule.

Bioactivity of an organic substance or a ligand is directly linked to the affinity of the ligand to the target receptor triggering the biological response. Little is still known about the biological role of chitinous compounds in the human body, although there are indications that chitin oligomers play a vital role in embryonic development. This suggests that the human genome is capable of expressing specific receptors which are specifically activated when binding to chitin oligomers. The only known chitin binding proteins in the human body, are the chitinase like proteins (CLPs), genetically belonging to the Family 18 chitinases, but most of them have lost their enzymatic activity.

The chitin binding domains in these proteins are highly preserved and do only differ from the active sides of the Family 18 chitinases by one or few amino adds. The binding of fully acetylated chitin oligosaccharides to the active site of the protein will generally induce a conformational change in the protein structure, indicating signaling role of the interaction. The current invention provides data showing that the binding side of one of the chitinase like proteins (YKL-40 or HC gp-39) possesses almost equally strong affinity (90%) towards the partially deacetylated T-ChOS compositions as compared to fully acetylated chitin oligosaccharides. Family 18 chitinases are highly active on chitinous substrates and require adjacent N-acetyl groups as a recognition site for hydrolysis and one of the acetyl groups will actively take part in the hydrolysis reaction as a proton donor. This suggests that chitin oligomers which are fully acetylated will be rapidly degraded in the human body (possess poor biostability), especially since chitinous structures are likely to induce expression of the corresponding endogenous Family 18 Chitinases. However, a partial deacetylation of the chitin oligomer will increase the biostability, especially if the partial deacetylation renders a sequence where there are no adjacent acetyl groups within the body of the oligomer. This would render a molecule which will not be cleaved by specific chitinolytic enzymes like Family 18 Chitinases, but will only be slowly degraded by less specialized enzymes capable of cleaving chitin as well as chitosan but with considerable lower specific activity. This suggests that the T-ChOS compositions possess the bioavailability, biostability and bioactivity required for therapeutic activity.

In a bone implant, the polymeric Chitobiomers will be gradually hydrolyzed by a macrophage derived Family 18 Chitinase, generating a large fraction of T-ChOS compositions. These highly soluble oligomers will diffuse throughout the composite and the adjacent tissues, acting as chemotactic factors or stimulants for macrophages as well as cartilage and bone progenitor cells located in the bone marrow as well as in the endosteum and the periosteum. This provides osteoinductivity to the bone implant composite.

The compositions of the present invention comprising therapeutic chitooligomers and their polymeric precursors (collectively referred to as Chitobiomers) are produced by a process which is based on several key processing steps that critically affect the composition and properties of the produced materials, such as solubility and purity. For maximum purity, an optional pre treatment step is provided whereby chitin from a suitable source is substantially dissolved in a suitable acid solution, preferably a mineral acid such as hydrochloric acid (HCl), although other acids may as well be used, including carboxylic acids and or mineral acids such as sulfuric acid, phosphoric acid or nitric acid. When HCl is used the concentration is typically about 15-37% (wt/wt) such as 25% or higher, concentration of other acids is adjusted appropriately to obtain similar results. In one embodiment, the acid-dissolved chitin is treated with an oxidant, preferably hydrogen peroxide although other oxidants may as well be used, e.g. alkali metal peroxides, alkaline earth and alkali metal perborates, percarbonates, peroxymonosulfates, persulfates, bromates, hypohalites and the dihalo-trazinetriones. The acidic dissolution of the chitin will open up its crystalline structure and expose endotoxin molecules embedded in the material, allowing efficient extraction and degradation of the endotoxin impurities. The optional oxidant treatment is intended to assist the degradation of the endotoxin molecules and thereby further reducing the endotoxin content of the final product. Some fragmentation of the polymer chains will occur at this step in the process. The solution of substantially dissolved chitin is preferably rapidly diluted and substantially neutralized with sufficiently pure water or alkaline aqueous solution, e.g., by streaming the solution with substantially dissolved chitin into a large volume of the neutralizing aqueous solution, such that a significant portion of the chitin material precipitates as amorphous colloidal chitin. The water is typically at an elevated temperature such as within the range of 40-100° C., e.g. in the range of 50-100° C., such as the range of 50-80° C. The temperature will affect the compactness and solidification of the colloidal chitin. After washing (preferably serial washings) in sufficiently pure water the colloidal chitin is ready for deacetylation.

In an embodiment of the present invention the partially deacetylated chitin and/or chitosan with the degree of deacetylation from 30-1000% DD, is mixed with calcium phosphate composites in order to regulate physico chemical, mechanical and biological properties of the final composite. This method is provided for controlling the mechanical and biological properties of a calcium phosphate composite by mixing Chitobiomers or chitosan of different degree of deacetylation into the composite. This provides a powerful tool for regulating crucial properties of the composite such as setting time, hardening time, hardness and strength as well as biodegradability and accessibility for migrating cells from the host tissue. This possibility of regulating these basic properties consists in the sharp decrease in water retaining capacity of the deacetylated chitin derivatives as the degree of deacetylation is increased from 30 to 100% DD, i.e. the lower the DD the higher the water retention capacity. Since the crystallization of the calcium phosphate involves reacting with water, the water availability in the composite will influence the crystal formation. The more water is retained by the partially deacetylated chitin, the smaller the crystals in the composite. This in turn will affect the mechanical properties and the biodegradability of the composite. The lower the degree of deacetylation (DD) of the Chitobiomer the easier it is for phagocytes such as macrophages to invade the composite matrix, opening up new pores for other migratory cells such as cartilage and bone progenitor cells as well as vascular endothelial cells. This is a crucial property since this will enhance the remodeling of the composite into a healthy functional tissue. Through optimization of the Chitobiomer in the deacetylation process it is possible to increase the yield of T-ChOS generated during the remodeling of the composite, providing effective stimulation of endochondral bone regeneration in a bone defect.

It is therefore concluded that by carefully controlling the degree of deacetylation of the partially deacetylated chitin used in the composite, it is possible to optimize the osteoconductivity as well as the osteoinductivity of the composite.

Deacetylation is typically carried out with the chitin raw material dissolved in the alkaline base reaction medium. This alkaline base is typically sodium hydroxide although other bases are as well suitable, including KOH, LiOH, $Ca(OH)_2$, $Na_3PO_4$ and $NH_4OH$. The ratio of dry matter to alkali may in some embodiments range from 1:5 to 1:100. The base solution is preferably cooled prior to the mixing. It has been found that by freezing the alkaline-chitin mixture and subsequently thawing and incubating for deacetylation, the homogeneity of the deacetylation will be substantially enhanced. The incubation temperature for the deacetylation process can however be adjusted within a relatively broad range of 0-100° C. and the incubation time is adjusted accordingly (lower deacetylation temperatures requires longer incubation times and vice versa). In some embodiments the deacetylation is conducted at a temperature in the range of 5-50° C., more preferably the range of 10-40° C. or in the range of 20-50° C., such as in the range of 10-30° C. or in the range of 10-25° C., and more preferably the range of 12-25° C., such as the range of 15-25° C. The partially deacetylated chitin is precipitated in sufficiently pure water, preferably at an elevated temperature, such as in the range of about 30-80° C., including the range of about 35-65° C., such as the range of about 45-60° C. or 40-50° C., and subsequently washed with sufficiently pure water. As described before, salt can be added to the solution to further assist in recovering the polymer in the precipitate. The material can subsequently be washed and may be freeze-dried or spray-dried, depending on the intended further use.

The described process renders significantly homogeneous deacetylation, which means that the N-acetyl-D-glucosamine residues (A) and glucosamine residues (D) in the polymer are substantially evenly distributed, influencing the subsequent hydrolysis of the polymer into therapeutic chitooligomers. This offers an opportunity to optimize the yield of T-ChOS during hydrolysis with a Family 18 Chitinase by carefully adjusting the average degree of deacetylation in the partially deacetylated chitin. Such hydrolysis could take place prior to use (i.e. In vitro, e.g. as described below) or in vivo by using the obtained polymeric precursor (Chitobiomer) as an ingredient in pharmaceuticals, biomaterials or medical devices. The chitobiomer will be slowly hydrolyzed by endogenous enzymes, e.g. such as chitotriosidase to generate therapeutic chitooligomers in situ.

As used herein the term "chaotropic agent" is an agent which causes molecular structure to be disrupted; in particular, those formed by nonbonding forces such as hydrogen bonding, Van der Waals interactions, and the hydrophobic effect. Often structural features, as detected by means such as circular dichroism can be titrated in a chaotrope concentration-dependent fashion.

The most commonly used chaotropes are 6~8M urea and 6M guanidinium chloride, with urea being an uncharged molecule and guanidinium chloride being a hydrochloride salt.

High generic salts can have chaotropic properties, by shielding charges and preventing the stabilization of salt bridges. Hydrogen bonding is stronger in nonpolar media, so salts, which increase the dipole moment of the solvent, can also destabilize hydrogen bonding.

In the present context the term "addition of a chaotropic agent such as a salt" refers to the addition of salts selected from, but not limited to NaOH, ammonium sulfate, urea, guanidinium chloride, Any salt of an acid, preferably a salt of tricarboxylic organic acid (for ex. citric acid) then a salt of dicarboxylic acid (malic acid) then a salt of monocarboxylic acid. A salt of high chaotropicity.

The obtained partially deacetylated chitobiomers have distinct features. The pre-dissolution of chitin, formation of colloidal chitin, and subsequent dissolution in alkaline base prior to deacetylation, significantly opens up the chitin crystalline structure and allows efficient reduction of bacterial endotoxins in the chitinous material, rendering polymer purity acceptable for use in biomaterial formulations and/or medical devices intended for implant applications.

The sequential pattern of the therapeutic chitooligomers directly affects their biological activity, i.e. how they are transported over biological membranes (bioavailability), how rapidly they brake down in living systems (biostability), and how they interact with chitinase like proteins and other specific receptors binding chitinous sequences (bioactivity).

Considering activity mechanisms of the Family 18 Chitinases, the recognition of a cleavage site in the substrate molecule requires a sequence of two or more adjacent N-acetyl-D-glucosamine moieties (-AA-). The cleavage leaves the two acetyl groups at the reducing end of the resulting product which means that if the enzymatic hydrolysis goes to completion, majority of the oligomers will have two N-acetyl-D-glucosamine moieties on the reducing end. This implies that a therapeutic chitooligomer of the invention with optimal bioavailability, biostability and bioactivity would be a partially acetylated chitooligomer with maximum acetylation without having two adjacent acetyl groups within the internal region of the molecule. A simple calculation would therefore suggest approximately 50% acetylation where the two monomers are alternating in their molecular sequence in the internal region (i.e. -DADADADA-). When this structure interacts with the binding domain of Family 18 chitinases, YKL-40 or any of its CLP relatives, the -DADADADA-structure has stronger affinity to the binding site compared to a predominant D sequence (i.e. -DDDDDA-). Same is true for the bioavailability of the therapeutic chitooligomers since increased acetylation increases the hydrophobicity of the molecule as well. This invention provides data showing that the binding affinity to CLP binding domain increases with the relative number of A residues ($F_A$). However, our data also establish that the T-ChOS compositions possess at least 90% of the binding affinity as measured for a fully acetylated chitin hexamer ($A_6$)

In the regard of bacterial endotoxin contamination, chitin and chitosan-derived materials intended for implant applications need specific attention, since exoskeleton-derived chitin as well as squid and cuttlefish derived chitin will typically contain substantial levels of bacterial endotoxins. In addition chitosan will gain significant affinity to bacterial endotoxins during and after deacetylation. Thus, any process intended to produce sufficiently pure chitosan for implant applications needs to incorporate specific steps to significantly extract and reduce bacterial endotoxins from the raw material substrate.

The pharmaceutical compositions described herein comprise the therapeutic chitooligomers (T-ChOS) of the invention. They can be administered systemically and bind to endogenous CLPs, many of which have been shown to or implied as playing a role in several diseases and conditions. Among the diseases and conditions that are associated with elevated expression of CLPs are degenerative diseases such as degenerative joint diseases including arthritis (e.g. rheumatoid arthritis and osteoarthritis). The T-ChOS compositions are found to be useful for treating and/or remedying these diseases as well as conditions relating to bone tissue formation and conditions such as bone regeneration after surgical interventions or trauma.

The composition may further comprise a pharmaceutically acceptable excipient such as processing aid or stability agents, diluents, flavorings, nutrients, or colorants or appropriate additional biologically active or non active ingredients.

The pharmaceutical composition shall preferably be in a form suitable for oral administration, such as a dry form which can be readily dissolved, e.g. in a glass of water. Such forms include dry powder, a suspension, a gel, a film, a foam, a sol, aerosol, granular, flake, fibrous and paste forms. However, the composition can also be contained in pills or capsules. The pharmaceutical compositions can further comprise a pharmaceutically acceptable excipient.

In other useful embodiments, the composition of the invention is in a form suitable for other forms of systemic administration, such as intramuscular, subcutaneous, or intravenous administration. Such suitable forms are solution forms with a pharmaceutically acceptable carrier or excipient according to standard pharmaceutical practice. Said solution forms are sterile, and the pH is suitably adjusted and buffered. For intravenous use, the total concentration of solute should be controlled to render the preparation isotonic.

The T-ChOS of the invention may conveniently be provided in an essentially dry form comprising a powder, flakes or fibrous material which can be delivered in capsules or tablets, or dissolved or suspended in an aqueous solution for intake. Such a composition may consist of substantially only the aforementioned therapeutic chitooligomers, i.e. In the range of about 80-100 wt % of the chitooligomers. In useful embodiments the composition comprises in the range of 20-100% by weight of said T-ChOS, including about 25-95 wt %, such as about 50-90 wt %.

Oral administration of the T-ChOS of the invention requires that the molecular structure of the T-ChOS fulfill several requirements; possess adequate bioavailability, i.e. be transported quantitatively across biological membranes in the gastrointestinal tract; have adequate biostability in order to survive initial degradation in the GI tract, and be distributed efficiently in the body fluids before being degraded and eliminated from the system, and finally they have to possess the appropriate bioactivity through binding to the target receptors. Fulfilling all these requirements demands a compromise where some or all criteria are only fulfilled on a suboptimal level. This requires a holistic view on the product optimization concept in order to obtain the best possible composition capable of overcoming the hurdles of absorption and biodegradation ensuring that the T-ChOS reach and interact with the target receptor(s).

In the present context the term "medical device" generally refers to an instrument, apparatus, implement, machine, contrivance, implant, in vitro reagent, or other similar or related article, including a component part, or accessory which is intended for use in the diagnosis of disease or other conditions, or in the cure, mitigation, treatment, or prevention of disease, in humans or other animals, or intended to affect the structure or any function of the body of humans or other animals. In the context herein, the term "biomaterial product" is used interchangeably with the term "medical device".

The chitobiomers (polymers and oligomers) of this invention are particularly useful in biomaterials for various purposes. Besides exhibiting all advantageous features of conventional chitosan (biocompatibility, ability to mix with other components to produce suitable mixtures for medical devices, such as mechanical implants, drug delivery devices etc.), they possess significantly increased solubility and biological or therapeutic activity due to their high affinity to CLPs in the body, as described above.

Formulation of the biomaterials can suitably include other organic and inorganic components such as various biopolymers (alginates and other polysaccharides etch), collagen, calcium phosphates, including hydroxyapatite, calcium sulfate, sodium tripolyphosphate, sodium dihydrogen phosphate, sodium glycerol phosphate, calcium oxide, calcium hydro oxide and various organic or carboxylic acids etc.

The biomaterials of the invention are useful in various medical devices that benefit from the properties of the Chitobiomers comprised in a biomaterial composition.

In the regeneration of bone and other tissues, there are two main types of bone, trabecular bone and cortical bone. Trabecular bone is spongy, and makes up the bulk of the interior of most bones, including the vertebrae, while cortical bone is dense and forms the surface of bones. The trabecular meshwork supports the blood-forming elements in bone.

The term "intramembranous ossification" refers to a process of new bone formation that originates from osteoprogenitor cells, which upon a proper triggering signal differentiate directly into new bone. This pathway of ossification takes place at the embryonic stage, especially in the growth of flat bones such as the cranial bones of the skull.

The term "endochondral ossification" refers to a bone forming process, whereby cartilage develops first yielding the framework of the final bone. The cartilaginous tissue needs less local oxygen tension for its development and maintenance than mature bone tissue and therefore, wherever the blood supply system has not attained its final stage of development cartilage will supersede bone. Cartilage will only be replaced by new bone after vascularization has reached its advanced stage, guaranteeing essential supply of oxygen to the developing tissues. This process of bone formation is also typical during the embryonic stage, particularly in vertebrae, long bones, sternum, etc.

EXAMPLES

Example 1

Production of Highly Pure Partially Deacetylated Chitin Polymer (Chitobiomer)

1.1 The Use of Homogeneous Deacetylation Condition in Order to Increase the Yield of Chitobiomer Compositions and Substantially Reduce the Level of Bacterial Endotoxins During Deacetylation Chitin powder (1) was added (2) to 50% NaOH (3) at 15° C. (ratio of chitin/NaOH, 1:15, w/w) and mix at constant speed of 36 rpm (4) for 1 h (5). Subsequently, fine crushed 3-10 mm ice (ratio alkali/ice, 1:3, w/w) (6) was added to the alkali slurry to dissolve the chitin. After 2 h when the chitin was dissolved and bacterial endotoxins fully exposed to the alkaline solution, temperature (7) was increased and deacetylation reaction carried out at 16° C. for 40 h. After deacetylation process is completed, and endotoxins are dramatically reduced (<30 EU/g), pH was further adjusted to 3.8 (8). This was followed by series of filtration steps (9) to remove foreign particles and undissolved polymers. The polymer was recovered by precipitation through a salting out method. After the recovery, the polymer was washed and homogenized. Finally the suspension was spray-dried (10) to obtain the purified polymer. This process is commercially feasible and will increase the yield of fully soluble Chitobiomer compositions by 60% compared to heterogeneous deacetylation process. Endotoxin levels will be dramatically reduced during the process, probably because endotoxin molecules will be more exposed to the caustic soda solution compared to the situation in a heterogeneous deacetylation process where the chitin raw material maintains its crystalline structure throughout the process and endotoxin molecules which might be locked into the solid chitin structure will probably gain protection from the caustic soda in the reaction medium.

Notes Numbers in Parenthesis Represent Method Steps that can be Varied According the List Below (1) The particle size of the powder may be 2 mm and below. Sources of chitin, including shrimp, crab, cuttlefish, squid, krill and others are suitable.
(2) Reactor that meet the hygienic requirement
(3) The final concentration of the alkali may range from 5 to 90% (w/w). The most favorable alkali is sodium hydroxide. Other alkali are as well suitable, these include concentrated KOH, LiOH, Ca(OH)$_2$, Na$_3$PO$_4$ and NH$_4$OH. The ratio of dry matter to alkali may range from 1:3 to 1:100. The temperature of the alkali may range from 2 to 35° C.
(4) The mixing speed may be varied from 0 to 80 rpm. The most favorable range is 20-40 rpm for this process
(5) The deacetylation time may range from 0.5 to 1000 h, mainly depending on the temperature and concentration of the alkali.
(6) The size of the crashed ice may range from 0.5 to 50 mm. The ratio of alkali to ice may range from 1:1 to 1:30
(7) The deacetylation temperature may range from 10 to 100° C., with optimum between 5-30° C. and the deacetylation time may range from 0.1 to 1000 hours. Depends depending on the combination of temperature and time that is applied.
(8) Various acids may be used for this acidification process, these include concentrated carboxylic acids and concentrated mineral acids. The most favorable is the hydrochloric add. The concentration of HCl may range from 0.01 to 37% (w/w)
(9) Various filtration technology may be applicable, including ultra-filtration and nanofiltration
(10) Drying may be done by freeze-drying or spray-dryer, or any other appropriate drying technology 1.2 Pretreatment of the Chitin Raw Material with Hydrochloric Acid in Order to Further Enhance the Reduction of Bacterial Endotoxins This example provides an additional step of pre treatment of the chitin raw material, involving dissolution of chitin powder in a strong hydrochloric acid (HCl) medium, efficiently extracting bacterial endotoxins from the dissolved chitin structure and subsequently destroying exposed endotoxins that are in contact with the HCl and an optional oxidative agent (e.g. hydrogen peroxide). Furthermore, during a subsequent liquid state deacetylation process, the dissolved chitin in the alkali allows further extraction and destruction of the endotoxins that survived the HCl treatment. This method is particularly useful in treating raw materials that have lost its freshness and been exposed to bacterial growth during harvesting, storage or transport.

Example of a Detailed Manufacturing Process

Powdery chitin (<150 μm) (1) was dissolved in 30% hydrochloric acid (2) at room temperature (ratio of chitin/HCl: 1:20, w/w). After 10 minutes, hydrogen peroxide was added (final concentration of H$_2$O$_2$, 2%, w/w) (3) and was allowed to react for 15 (4) minutes, then the solution was streamed into a 75% IPA (chitin solution:50% IPA solution was 1:40)(5) and washed to a neutral pH. Then the precipitate was washed additionally with endotoxin-free water at 70° C. (6). After removing excess water, concentrated alkali solution (final concentration of alkali was 250% w/w) (7) was added to the colloidal chitin. Then the mixture was brought to −25° C. (8). This was followed by defrosting and dissolving the colloidal chitin and deacetylating at 60° C. for 6 h (9). After the deacetylation, the partially deacetylated chitin was recovered by pouring it into hot water (70° C.) (10) and wash to a neutral pH. Finally, the neutralized suspension is transferred to a freeze-dryer/spray-dryer to obtain the dry matter.

The endotoxin level of the obtained chitobiomer product is generally well below 30 EU/g partially deacetylated chitin by LAL analytical method.

1.3 Purification of Partially Deacetylated Chitin Solution and Polymer Recovery Through a Salting Out Method The compositions of the invention may suitably be obtained from chitinous raw material such as shrimp shells. Chitin is advantageously deacetylated with a strong base, to obtain a partially deacetylated chitin polymer. Or subsequently, the material can be the product according to 1.1 or 1.2 in this Example, in order to increase the yield of soluble Chitobiomers and reduce bacterial endotoxin (EU) levels before the purification. The time of the reaction and concentration of chitin may be varied depending on the desired degree of deacetylation, and can readily be optimized for any particular processing unit and a particular desired degree of deacetylation. The deacetylation reaction is halted by pH neutralization, either by washing the obtained partially deacetylated chitin with hot water or by adding suitable acid. Purification may then be applied by dissolving the obtained polymer in an acidic solution and filtering the solution in order to remove foreign or insoluble materials.

To recover the partially deacetylated chitin polymer, the temperature of the filtered solution is first increased to above 55° C. Then the pH is adjusted to above 8, preferably pH 10-11 and finally a suitable salt is added to initiate the precipitation process. Then hot water is used to wash the precipitate until a neutral and salt-free material is obtained. After the washing process, appropriate conventional drying method(s) may be applied to dry the material.

This example teaches how highly soluble partially deacetylated chitin (average degree of deacetylation between 30 and 55%) can be recovered from such a filtered polymer solution without using organic solvents. The optional addition of salt (NaCl) is to enhance the compactness of the precipitate for a easier recovery in a commercial process.

Selected Examples 1.3.1 One g of 43% DD partially deacetylated chitin (Lot G060307P) was dispersed in 100 g of water. Citric acid (2 g) was added to dissolve the polymer. Temperature was increased to 60° C. and NaOH (35% solution) was added dropwise to adjust the pH to 11. This resulted in a precipitation of the polymer which could be washed with hot water to near neutrality.

1.3.2 in a pilot-scale experiment (Lot G060307P) with 1 kg of chitin, the chitin was first deacetylated, washed and dissolved in 1% citric acid solution. This was followed by multiple-step filtration to obtain a clear solution. After heating to 65° C., 350 g of NaOH was introduced to adjust the pH to 10.5. Subsequently 4.5 kg of NaCl was added, introducing formation of white lumps of precipitate. The precipitate was washed intensively with 70° C. water until neutral pH was obtained. The precipitate was then homogenized and spray-dried to produce white powdery partially deacetylated chitin. The preparation was analyzed as follows:

Average particle size of the dried powder was 5 µm (with a distribution of 3-10 µm), degree of deacetylation was 43%, apparent viscosity was 540 cps (1% product in 1% acetic add), turbidity (1% product)<15 NTU.

FIG. 1 illustrates the solubility of this product (43% DD) compared to 70% deacetylated and 94% deacetylated chitosan. The 43% DD polymer was fully soluble at physiological pH 7.4 (no changes in turbidity). The 70% DD polymer was partially soluble at pH 7.4 but the 94% DD chitosan polymer was precipitated (turbidity >1000 NTU).

The results show that by dissolving the chitin polymer in alkali and ice, a homogenous deacetylation can be performed such that the distribution of remaining N-acetyl-glucosamine can be controlled. The experiments also show that this can be done on an industrial feasible scale and that this deacetylation method can be used to increase the yield of T-ChOS in a chitooligomer preparation obtained by applying chitinase.

Example 2

Production and Characterization of T-ChOS 2.1 Production of Lot G020418; A Heterogeneous ChOS Test Lot; Quantification and Sequencing of Homologues Production Sodium hydroxide, 25 kg was dissolved in 25 kg of water in an 80 L blender and heated to 60° C. Shrimp chitin from *P. borealis* (Genis ehf.), 2.5 kg was added and stirred (15 rpm) for 40 min. The slurry was then cooled with water and washed in a cheesecloth bag (200×40 cm) for 10-15 minutes. The chitin gel was transferred into a 200 L blender, the pH was adjusted to 4.0 by addition of 30% HCl, and water was added to give a volume of 100 L. A Family 18 endo-chitinase was added (10,000 units/kg substrate) the gel was stirred for 22 hrs at 30° C. The enzyme was denatured by adjusting the pH to 5.4 and heating of the solution to 80° C. for 10 min. After cooling, the oligomer solution (ChOS) was poured through a sieve of 280 µm mesh size. The solution was desalted using DSS LabStak M20 nanofiltration unit with 0.72 cm$^2$ of 500 Da cut-off membranes at pH 4.8. The solution was then subjected to spray drying, using a rotary atomizing spray-drying unit at an inlet air temperature of 190° C. and an outlet air temperature of 80° C. The fine white ChOS powder, 2.0 kg (80%) was collected and kept at room temperature. Degree of deacetylation was 37% (or $F_A$ 0.63) as judged by direct titration.

Analytical Methods

BioGel P4 Gel Permeation Chromatography Analysis (GPC)

Quantity 2.16 g of the ChOS powder was dissolved in 180 mL of 0.05 ammonium acetate buffer at pH 4.2. The resulting solution was filtered sequentially through a 0.8 µm, and a 0.2 µm cellulose acetate membrane (Schleicher & Schuell), and a ultrafiltrated through a 3000 Da cut-off membrane (Amicon). The filtrate was lyophilised. The yield was 0.74 g (34%). The resulting powder (lots of 350 mg) were then separated by gel permeation chromatography (GPC) on Biogel P4, fine grade (BioRad, München, Germany). Column dimension: 5×200 cm; mobile phase 0.05 M ammonium acetate buffer, adjusted with 0.23 M acetic acid to pH 4.2; flow rate 60 mL/hour; Refractive index detector Shimadzu RID 6A. Fractions of 20 ml were collected, appropriately combined, concentrated to a small volume and finally lyophilized.

Preparation of Homologues—Ion Exchange Chromatography 4 mg of lyophilised fractions from GPC were dissolved in 200 µL of aqueous hydrochloride at pH 3.0. The solution was filtrated through a 0.45 µm syringe filter with Nylon membrane (Nalgene). The homologues were separated by high performance ion exchange chromatography (HP-IEC) on Resource S (Amersham Pharmacia Biotech, Sweden). Bed volume: 1 ml; mobile phase: aqueous hydrochloride of pH 3.0 (A), 1 M aqueous sodium chloride solution of pH 3.04 (B); elution profile: 0-5 min 100% A, 5-45 min 100%-50% A, 45-46 min 50%-0% A, 46-55 min 0% A, 55-56 min 0%-100% A, 56-80 min 100% A; flow rate 60 mL×h$^{-1}$; UV detector Jasco UV-MD-910. Fractions of 500 µL were collected, appropriately combined, dialyzed in Floatalyzers™ (SpectraPor) against water (2 L, 4 days), concentrated to a small volume and finally lyophilised. The sample was subjected in batches of 4 mg to HP-IEC. For yields see Results and Discussion.

Reductive Amination of ChOS with 2-Aminoacridone (AMAC)

30 nmol of pure ChOS or 60-80 nmol of the ChOS mixture was dissolved in 20 µL of a 0.1 M solution of 2-aminoacridone in acetic acid/DMSO (v/v 3:17) and agitated manually for 30 s, followed by addition of 20 µL of a 1M solution of sodium cyanoborohydride in water and further agitation for 30 s. The mixture was heated in the dark for 30 min at 90° C. The reaction vessel was cooled to −20° C., and the reaction mixture was lyophylized. The residue was dissolved in 1 ml of water, dialyzed against 1 L of water for 48 h and finally lyophilised to give a light yellow powder. The samples were either analyzed immediately or stored in the dark at −20° C.

Mass Spectrometry

The lyophilized AMAC-oligosaccharide derivatives were redissolved in 200-500 µL of methanol/water (v/v 50:50). An aliquot of the solution (0.5 µL) was mixed on the target with 2 µL of a solution of DHB as a matrix (15 mg×mL$^{-1}$) in 30% aqueous ethanol, and the drop was dried under gentle stream of air. Crystallization of the matrix occurred usually spontaneously. In some cases, crystallization was observed only after diluting the original sample solution ca. 5-fold with methanol/water (v/v 50:50).

MALDI TOF mass spectra were recorded on a Bruker Reflex II (Bruker Daltonik, Bremen, Germany) in the positive ion mode. For ionization, a nitrogen laser (337 nm, 3 ns pulse width, 3 Hz) was used. For optimization of the mass spectra, the laser was aimed either at the central area of the sample or at the outmost edge of the crystal rim. All spectra were measured in the reflector mode using external calibration (Angiotensin II).

Sequencing of ChOS Homologues—Isobars

All homologues of DP3 to DP8 that showed an appropriate signal in the MALDI TOF mass spectrum were sequenced following a procedure described in details elsewhere[1]. Briefly, 60-80 nmol of each lyophilised GPC fraction F3-F10 were reductively aminated with 2-aminoacridone giving homologues tagged at the reducing end[2]. (MALDI TOF mass spectrum of GPC fraction F7-AMAC see below, others not shown). The fractions were analysed by MALDI tandem mass spectrometry. Monosodiated pseudomolecular ions of homologues of interest were selected in the quadrupole of the mass spectrometer and fragmented in the collision cell leading to A-, B- and C-type ions, which are formed from the nonreducing end, and X-, Y- and Z-type ions from the reducing end. Due to the tag at the reducing end Y-type ions could be identified by the mass increment of 194 Da, and the oligosaccharide sequence could be readout from the reducing end using a sequence tree.

Results

Table 1 shows the DP of each ChOS and homologues of each fraction as well as the mass distribution of fractions F1-F10. Table 2 shows the sequences of isobars, which were found by sequence analysis of the homologues of the ChOS.

For the main compounds of the ChOS between DP5 and DP7 these results could be quantified (D2A3, D3A3, D2A4, D3A4).

To obtain quantitative information about a mixture of isobars pseudo MS had to be employed: The sample is fragmentized in the source (without preselection of an ion), a fragment ion is selected in the quadrupole of the mass spectrometer, fragmentized in the collision cell, and the mass spectrum of the last fragmentation is recorded.

As the first fragmentation is carried out without any preselection of ions, the sample has to be a pure homologue. Especially, no ions with lower masses than the analyte should be present in the MALDI TOF mass spectrum.

For that reason it was necessary to purify the GPC fractions previous to quantitative sequence analysis. The homologues of GPC fractions F6 to F9 were separated by charge number on a cation exchange HPLC column to give pure D2A3 (F6), D3A3 (F7), D2A4 (F8) and D3A4 (F9). Table 3 collects the results of the HP-IEC separations of GPC fractions F6 to F9.

The pure homologues D2A3, D3A3, D2A4 and D3A4 were reductively aminated with 2-aminoacridone giving derivatives tagged at the reducing end (MALDI TOF mass spectrum of D3A3-AMAC see below, others not shown). The derivative homologues were sequenced as described above by pseudo MALDI MS.

Figure 2:
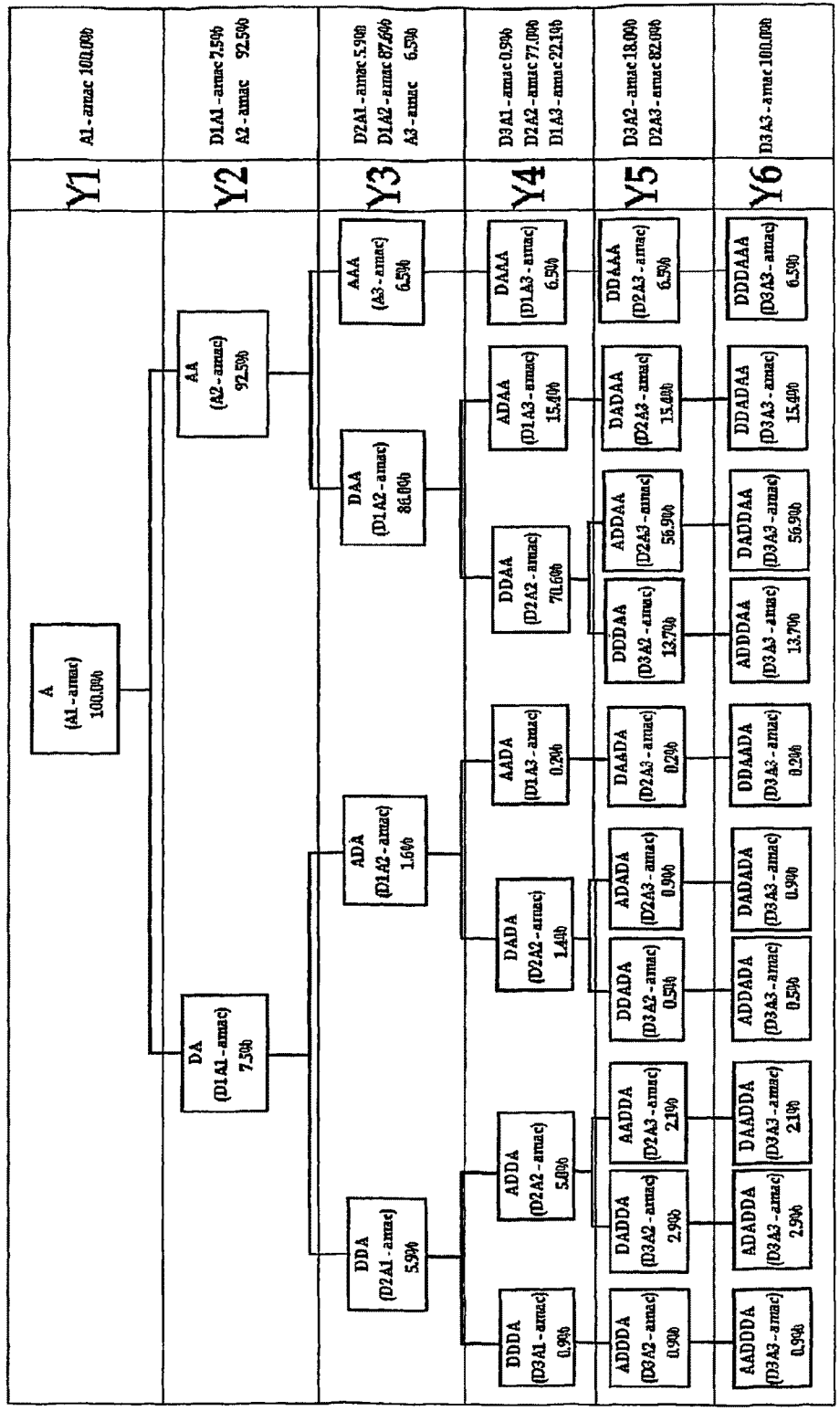
Figure 3:
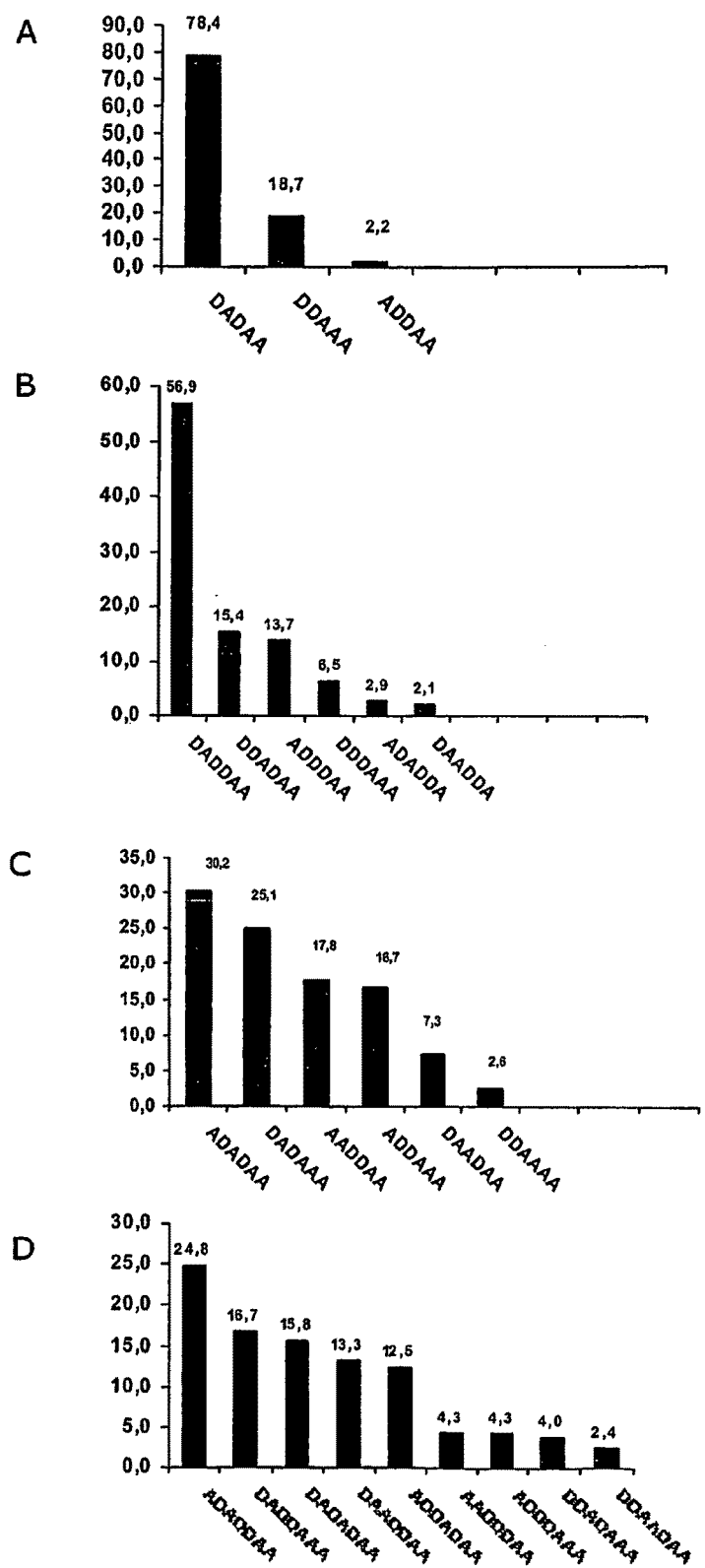

The relative intensities [%] of the homologue fragment ions were assigned by the evaluation software. The reproducibility of the relative peak intensities was proved by repeated fragmentation. The average standard aviation was found to be 1%. FIG. 2 shows the sequence tree for D3A3 quantifying the intensities of peaks caused by fragment ions of different sequences. For the Y2-type ions the relative amounts of DA (7.5%) and AA (92.5%) could be directly read out from the relative peak intensities of D1A1-AMAC and A2-AMAC.

For the Y3-type ions the relative amounts of DDA (5.9%) and AAA (6.5%) could be directly read out from the relative peak intensities of D2A1-AMAC and A3-AMAC. The relative amount of ADA (1.6%) could be concluded from the equation [DDA]+[ADA]=7.5%, that one of DAA (86.0%) from the equation [DAA]+[AAA]=92.5%.

For the Y4-type ions the relative amount of DDDA (0.9%) could be directly read out from the relative peak intensity of D3A1-AMAC. The relative amount of ADDA (5.0%) could be concluded from the equation [DDDA]+(ADDA)=5.9%. The relative amount of DAAA is 6.5% as only DAMA-AMAC gives A3-AMAC, which was assigned with a relative peak intensity of 6.5%.

TABLE 1

Composition and mass distribution of ChOS fractions F1-F10.

| GPC Fraction | Yield[a] [%] | Oligomers | Homologues |
|---|---|---|---|
| F1 | 16.3 | DP1 | A1 |
|  |  | DP2 | A2 |
| F2 | 22.2 | DP2 | A2 |
|  |  | DP3 | D1A2 |
| F3 | 24.6 | DP2 | A2 |
|  |  | DP3 | D1A2, A3 |
|  |  | DP4 | D3A1, D2A2 |
| F4 | 11.2 | DP3 | D1A2, A3 |
|  |  | DP4 | D2A2, D1A3 |
| F5 | 13.1 | DP3 | A3 |
|  |  | DP4 | D2A2, D1A3 |
|  |  | DP5 | D3A2, D2A3 |
| F6 | 4.5 | DP3 | A3 |
|  |  | DP4 | D1A3, A4 |
|  |  | DP5 | D3A2, D2A3, |
| F7 | 3.3 | DP4 | D1A3, A4 |
|  |  | DP5 | D2A3, D1A4 |
|  |  | DP6 | D3A3, D2A4 |
| F8 | 2.3 | DP5 | A5 |
|  |  | DP6 | D4A2, D3A3, |
|  |  | DP7 | D4A3, D3A4 |
| F9 | 1.6 | DP6 | D2A4, D1A5 |
|  |  | DP7 | D5A2, D4A3, |
| F10 | 0.9 | DP7 | D4A3, D3A4, |
|  |  | DP8 | D5A3, D4A4, |
|  |  |  | D3A5 |
|  |  | DP9 | D6A3, D5A4 |

GPC separation on Biogel P4. The yield is calculated from masses of the dialysed and dried fractions.

TABLE 2

Sequences of isobars referring to homologues of the ChOS.

| DP | Homologue | Sequence[a] | Number of Isobars[b] |
|---|---|---|---|
| DP3 | D1A2 | DAA | 1 (3) |
| DP4 | D2A2 | (DDA)A | 3 (6) |
|  | D1A3 | (DA)AA | 2 (4) |
| DP5 | D3A2 | D(DDA)A | 5 (10) |
|  |  | D(DA)AD |  |
|  | D2A3 | (DDAA)A | 6 (10) |
|  | D1A4 | A(DA)AA | 2 (5) |
| DP6 | D4A2 | D(DDDA)A | 4 (15) |
|  | D3A3 | (DDDAA)A | 10 (20) |
|  | D2A4 | (DDAAA)A | 10 (15) |
|  | D1A5 | (DAAAA)AA | 4 (6) |
| DP7 | D4A3 | (DDDDA)AA | 18 (35) |
|  |  | (DDDA)A(DA) |  |
|  |  | (DDA)AD(DA) |  |
|  | D3A4 | (DDDAA)AA | 20 (35) |
|  |  | (DDAAA)DA |  |
|  | D2A5 | A(DA)(DA)AA | 4 (21) |

TABLE 2-continued

Sequences of isobars referring to homologues of the ChOS.

| DP | Homologue | Sequence[a] | Number of Isobars[b] |
|---|---|---|---|
| DP8 | D5A3 | D(DDDDA)AA | |
| | | D(DDDA)ADA | 12 (36) |
| | | D(DDA)ADDA | |
| | D4A4 | D(DA)(DDA)AA | |
| | | D(DA)(DAA)DA | 15 (70) |
| | | DAAD(DDA)A | |
| | D3A5 | AADD(DA)AA | 10 (56) |
| | | (DA)(DA)(DA)AA | |

Product G020418.
[a]sequence in bracket means permutation position: (DDA)A is equivalent to DDAA and DADA and ADDA. The reducing end of each sequence is shown at the right hand side.
[b]number in brackets gives the calculated maximum number of isobars for a homologue $D_N A_M$: $(N + M)!/(N! \times M!)$

TABLE 3

Composition and mass distribution of fractions of homologues after separation of fractions from GPC on a cation exchange column (Resource S). Product G020418.

| GPC fraction | Yield[a] [%] | HPIEC Fraction | Homologues[b] | Yield[c] [%] | Yield[d] [%] |
|---|---|---|---|---|---|
| F6 | 78 | F6FI1 | A3, A4 | 14 | 9 |
| | | F6FI2 | D1A3, D1A4 | 25 | 24 |
| | | F6FI3 | D2A3 | 51 | 54 |
| | | F6FI4 | D3A2 | 10 | 13 |
| F7 | 82 | F7FI1 | A4 | 17 | 12 |
| | | F7FI2 | D1A3, D1A4 | 30 | 28 |
| | | F7FI3 | D2A3, D2A4 | 13 | 15 |
| | | F7FI4 | D3A3 | 40 | 45 |
| F8 | 71 | F8FI1 | A5 | 12 | 8 |
| | | F8FI2 | D2A4 | 42 | 47 |
| | | F8FI3 | D3A3, D3A4 | 35 | 31 |
| | | F8FI4 | D4A2, D4A3 | 11 | 14 |
| F9 | 73 | F9FI1 | A6 | 12 | 7 |
| | | F9FI2 | D2A4 | 40 | 37 |
| | | F9FI3 | D3A4 | 32 | 35 |
| | | F9FI4 | D4A3, D5A2 | 16 | 21 |

[a]Sum of the dry weights of all dialyzed HPIEC fractions that are listed in the table
[b]Analysis by MALDI TOF MS (MALDI TOF mass spectrum of D3A3 see below, others not shown)
[c]Yield as calculated from peak areas of UV detection (regarding that different numbers of acetyl groups in a molecule lead to different molar absorption coefficients)
[d]Yield as calculated from masses of fractions In the pseudo MS3 of D1A3-AMAC the relative peak intensities of D1A1-AMAC and A2-AMAC are 1.0% and 99.0%. In the MALDI tandem mass spectrum of D3A3-AMAC the relative peak intensity of D1A3-AMAC is 22.1%. AADA is the only sequence of D1A3 (AADA, ADAA, DAAA) giving the fragment D1A1-AMAC. For that reason the relative amount of AADA is 1% of 22.1%=0.2%. The relative amount of DADA (1.4%) could be calculated from the equation [AADA]+[DADA]=1.6%. The relative amount of ADAA (15.4%) could be calculated from the equation [MDA]+[ADAA]+[DAAA]=22.1%. Finally, the relative amount of DDAA (70.6) could be calculated from the equation [ADAA]+[DDAA]=86.0%. For the Y5-type ions the relative amount of ADDDA is 0.9% as only ADDDA-AMAC gives DDDA-AMAC, which was assigned with a relative peak intensity of 0.9%. Analogous considerations allow assignment of DMDA (0.2%), DADM (15.4%) and DDAAA (6.5%).

In the pseudo MS3 of D2A3-AMAC the relative peak intensities of D2A1-AMAC, D1A2-AMAC and A3-AMAC are 2.6%, 88.0% and 9.4%. In the MALDI tandem mass spectrum of D3A3-AMAC the relative peak intensity of D2A3-AMAC is 82.0%. AADDA is the only sequence of D2A3 (AADDA, ADADA, DAADA, ADDAA, DADAA, DDAAA) giving the fragment D2A1-AMAC. For that reason the relative amount of MDDA is 2.6% of 82.0%=2.1%. The relative amount of DADDA (2.9%) could be calculated from the equation [DADDA]+[AADDA]=5.0%. In the pseudo MS3 of D2A3-AMAC the relative peak intensities of D1A1-AMAC and A2-AMAC are 3.9% and 96.1%. ADDM, DADM and DDAAA are the only sequences of D2A3 giving A2-AMAC. For that reason the relative amount of ADDAA+DADAA+DDAAA is 96.1% of 82.0%=78.8%. From this equation the relative amount of ADDAA (56.9%) could be calculated. The relative amount of DDDAA (13.7%) could be calculated from the equation [DDDM]+[ADDM]=70.6%. The relative amount of DDADA (0.5%) could be calculated from the equation [DDADA]+[ADDDA]+[DADDA]+[DDDAA]=18.0%, that one of ADADA (0.9%) from the equation [DDADA]+[ADADA]=1.4%.

FIG. 3a-3d show the relative amounts of isobars of the homologues D2A3, D3A3, D2A4 and D3A4. Isobars were not included in the diagrams if the calculated amount was less than 1%, as the reproducibility of the method allows not determining relative peak intensities less than 1%.

2.2 Production of Lot G050421; an Improved Yield of T-ChOS by Homogeneous Deacetylation Process Production Homogeneous Chitooligosaccharides G050421

Deacetylation was performed as described in Example 1. After deacetylation process is completed, pH was further adjusted to 3.8 using hydrochloric acid, and temperature adjusted to 35° C. A Family 18 endo-chitinase (10,000 units/kg substrate) was added to the solution and the hydrolysis reaction was allowed to continue for 22 h to a complete hydrolysis. This was follow by series of filtration steps to remove solid particles and an ultrafiltration step to remove remnants of the enzyme protein and other polymers. Finally the solution was spray dried to obtain powdered therapeutic chitooligosaccharides (T-ChOS) (G050421).

Analysis Methods

GPC Fractionation on Biogel P4 was performed as previously described. MALDI-TOF Mass Spectrometry of GPC fractions was performed as previously described.

Results

The degree of deacetylation for the heterogeneous deacetylated ChOS was 39% and 40% for the homogeneous deacetylated oligomers (G050421) as judged by direct titration.

Figure 4:
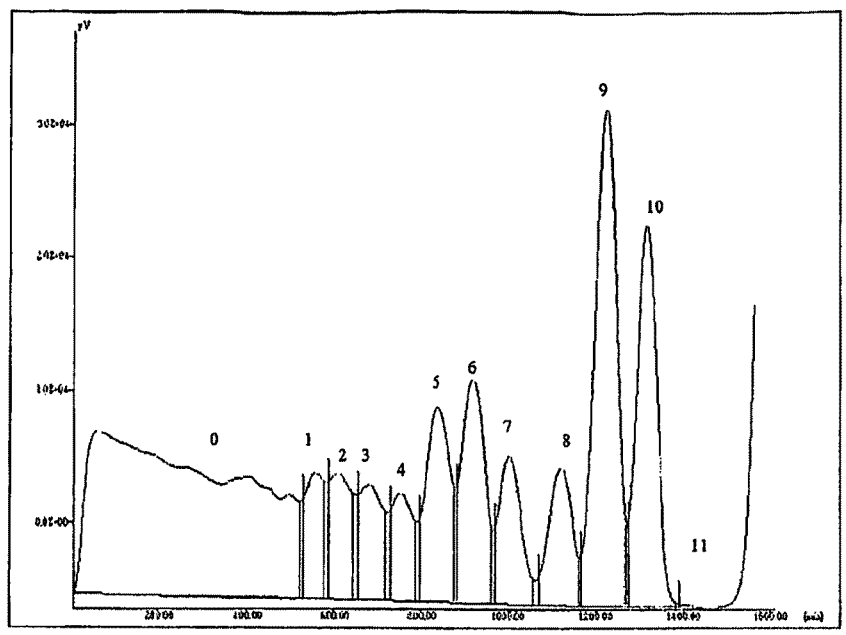
Figure 5:
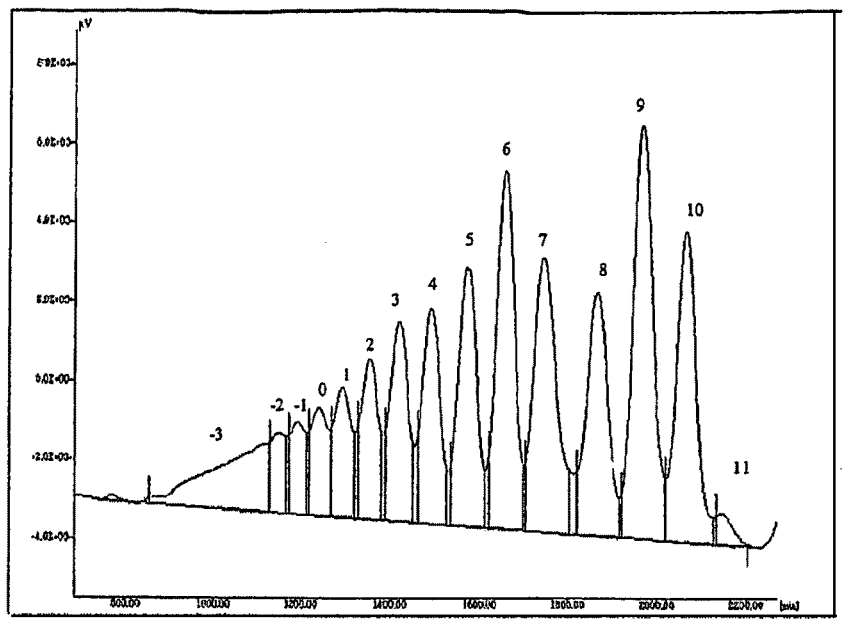

The oligomer peak distribution and homolog analysis for the heterogeneous deacetylated oligomers (G020418) is shown in FIG. 4 and for the homogeneous deacetylated oligomers (G050421) in FIG. 5. The most significant difference in peak distribution is observed for the longer oligomers. For the heterogeneous deacetylated oligomers, the DP11 to 22 (the peak area 0 in FIG. 4) is 35.5% of the total material and the quantity is increased with increased DP of 11 to 22. For the homogeneous deacetylated oligomers, on the other hand, the DP 11 to 22 (the peak area 0 to −3 in FIG. 5) is only 12.9% of the total material and the quantity is decreased with increased DP11 to 22, leaving literary no DP18 or higher. This is also reflected in the value of highly active oligomers (DP5-10). The homogeneous oligomers have 41% DP5-10 but the heterogeneous oligomers only 28% DP5-10.

Figure 6:
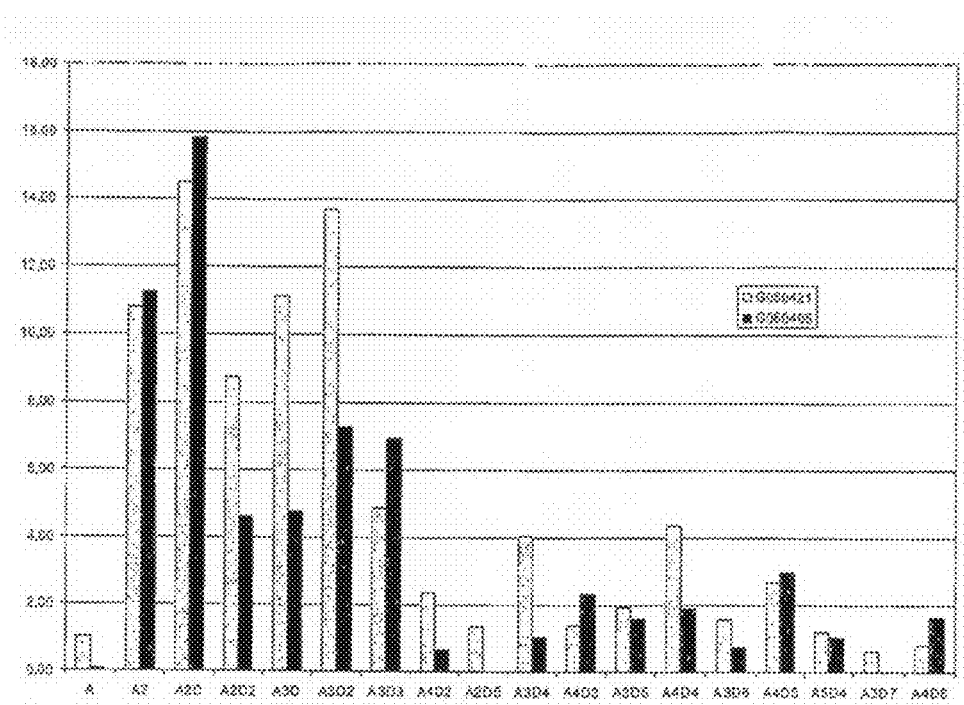

The homolog distribution is indicated in FIG. 6 for the oligomers by these two methods of deacetylation. For heterogeneous oligomers there is much less of DP4 ($A_2D_2$ and $A_3D$) and DP5 ($A_3D2$) as well as DP7 ($A_3D_4$) and DP8 ($A_4D_4$) than for the homogeneous oligomers (FIG. 6).

In summary the method of homogeneous deacetylation for is much likely to give ChOS of higher bioactivity than the heterogeneous deacetylation. A significant decrease in the production of the unwanted higher DP>15 oligomers is observed by this method.

2.3 Enhancement of the Relative Amount of T-ChOS by Ultrafiltration (lot G051128)

To improve the relative amount of T-ChOS (DP5-15) an additional ultrafiltration step was performed where the T-ChOS solution was filtered and concentrated on a 1 kDa UF membranes (Helicon, Millipore) where small chitooligomers (DP 2-5) are greatly reduced and monomers eliminated. The permeate was discarded and the retentate was collected and spray dried.

For analysis of test material, HPLC was applied using Beckman Gold system. TSK-oligo column (TosoHaas, Japan), separating the ChOS by molecular weight (DP1, DP2 etc.) was used. The solvent was 5 mM ammonium hydroxide, pH 10.0, flow rate was 0.5 ml/min, optical absorbance was 205 nm, injection volume was 20 µl and ChOS concentration was 10 mg/ml.

Figure 7:
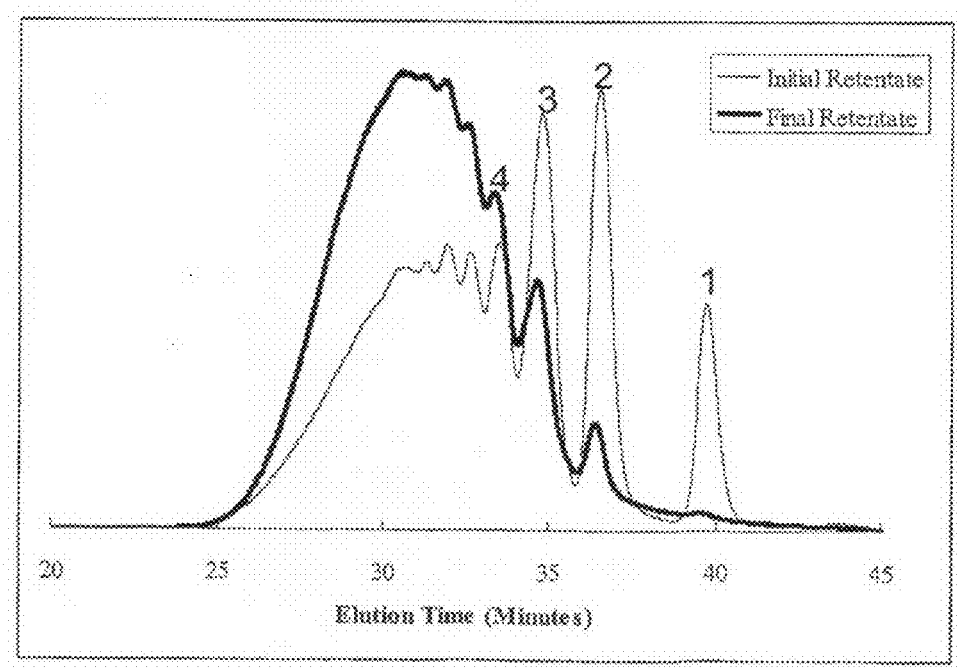

FIG. 7 shows the relative amount of each DP before and after the ultrafiltration step. Monomer has been eliminated and smaller oligomers (DP2-5) significantly reduced.

Example 3

Absorption of Therapeutic Chitooligosaccharides in the Human Body

Methods
Chitooligomers

Chitooligomers composed of N-acetyl glucosamine and glucosamine were prepared by Genis, Reykjavik, Iceland. Briefly, chitin was partially deacetylated in alkali, washed and hydrolysed to oligomers by chitinase. Oligomers were ultrafiltrated, desalted and spray dried to a fine white powder. Average degree of deacetylation was 47% ($F_A$ 0.53). Analysis and quantification of oligomers and homologues were performed, using the same methods as for the blood. This data was used to compare the absorption of different homologues into the blood.

General Blood Sample Treatment

A voluntary subject was consuming daily 1.8 g of ChOS (Genis ehf; S41124-1K) for a period of 4 weeks. Blood samples were collected within a period of 6 weeks. The first sample was taken before consumption of ChOS. The following 4 samples were taken weekly starting 1 week after the first consumption. Sample 6 was taken 2 weeks after stopping the consumption of ChOS. The volume of each sample was 7.0 ml. The blood samples were centrifuged for 30 min at 3000 rpm. The serum was collected. Methanol and sodium chloride were added to a final concentration of 30% methanol and 0.1 mg/ml sodium chloride followed by another centrifugation step. Samples of 500 µl were filtered through 3 kDa cut-off membranes (ultrafiltration). The supernatant was filled up for 3 times. Appropriate filtrates were pooled, the methanol was removed in vacuum, and the samples were finally lyophilised.

MALDI-TOF MS

The lyophilised samples (app. 100 µg) were redissolved in 100 µl of methanol/water (v/v 50:50). An aliquot of the solution was mixed on the target with 2 µl of a solution of DHB in 30% aqueous ethanol (15 mg*mg$^{-1}$). The drop was dried under a gentle stream of air. Mass spectra were recorded on a Bruker Reflex II (Daltonik, Bremen, Germany) in the positive ion mode. For ionisation, a nitrogen laser (337 nm, 3 ns pulse width, 3 Hz) was used. All spectra were measured in the reflector mode using external calibration. Monoisotopic peaks are labelled in all mass spectra.

Homologue Determination by MALDI-TOF MS

The lyophilised samples (appr. 100 µg) were redissolved in 100 µl of methanol/deuterium oxide (v/v 50:50). A 10-fold molar excess of hexadeutero acetic anhydride was added as well as 3 drops of glacial tetradeutero acetic acid. The solution was stirred at 30° C. for 12 h. The reaction was stopped by addition of an equimolar amount of ammonia. The solutions were lyophilised and redissolved in 100 µl of ammonia. The concentration of ammonia was set to a 10-fold molar excess with respect to the moles of N-acetyl glucosamine units (GlcNAc or A). The solution was stirred at 22° C. over night. The ammonia was removed in vacuum, followed by lyophilisation of the samples. In case that the MALDI-TOF MS still showed O-acetyl groups, the lyophilisate was redissolved in aqueous sodium hydroxide (100 µl). The concentration of potassium hydroxide was set to a 2-fold molar excess with respect to the moles of GlcNAc units. The solution was stirred for 10 h at r. t. neutralized by addition of cation exchange resin (H$^+$ form) followed by filtration and lyophilisation of the filtrate.

MALDI-TOF mass spectra were taken as described in Example 4. The quantification of relative signal intensities leads to the composition of homologues in the mixture.

Quantitative Determination of ChOS by MALDI-TOF MS

The samples are prepared as described under Homologue determination by MALDI-TOF MS. Subsequently, a standard was added to each sample. The standard, a chitin oligomer ($A_n$), has to be of the same DP+/−1 as the analyte. A serial dilution of this standard was used. A comparison of the signal intensities of the analyte with the standard gives the concentration of the analyte.

Gel Permeation Chromatography (GPC)

Oligomers were separated employing GPC on Biogel P4 as described in Example 2. Appropriate fractions were combined; the volume was reduced in vacuum followed by lyophilisation up to constant mass to remove the ammonium acetate.

High Performance Ion Exchange Chromatography (HPIEC)

Mixtures of homologues (and oligomers) obtained from the GPC separation were analysed by HPIEC. Conditions: Stationary phase: Resource S (Pharmacia, Uppsala, Sweden), bed volume 1 ml; mobile phase: hydrochloric acid pH 3.5, sodium chloride gradient 0-1 M from 5-60 min, flow rate 1 ml/min; equipment: HPLC instrument (Jasco, Gross-Umstadt, Germany) with UV detector (detection wavelength 210 nm). The HPLC fractions were lyophilised. Occasionally, the fractions were desalted by dialysis (Floatalyzer®, SpektraPor, Germany).

Quantitative Determination of Homologues by Means of HPIEC

The experiments were essentially performed as described under High Performance Ion Exchange Chromatography. A standard was added to each sample. The standard has to be within the same range of concentration as the analyte. The concentration of the analyte is calculated from the comparison of the peak areas of the standard and the analyte. Peak areas show a linear correlation to the number of acetyl groups in the analyte molecule.

Results

The MALDI-TOF MS of the blood sample collected before consumption of ChOS did not show any signals of ChOS.

Post 1 Week

In the blood sample post 1 week of ChOS consumption, only traces of DP2 (A2 homologue) and DP3 (D1A2 homologue) of the oligomers were observed (data not shown).

Post 2 Weeks

Figure 8:
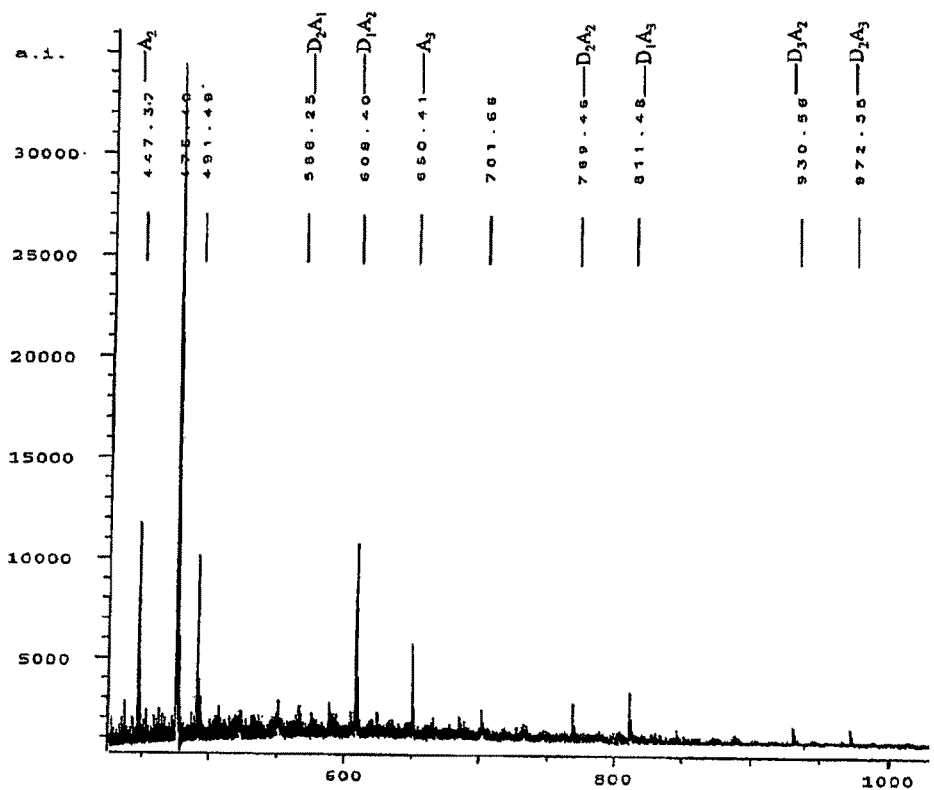

The blood samples taken after 2 weeks of ChOS consumption showed clear signs of heterochitooligomers as judged by the MALDI-TOF mass spectra. FIG. 8 shows homologues of DP2-DP5; Homologues of DP2 (homologue A2) up to DP12 (homologue D7A5) were clearly spotted in the mass spectras. Quantitative determination of homologues by various methods (see the Method chapter) revealed the total ChOS concentration of 0.16 mg/ml serum after 2 weeks of consumption. Assuming the total blood volume to be 5 L the total amount of ChOS absorbed is 0.80 g or 44% of the daily dose.

Post 3 Weeks

Figure 9:
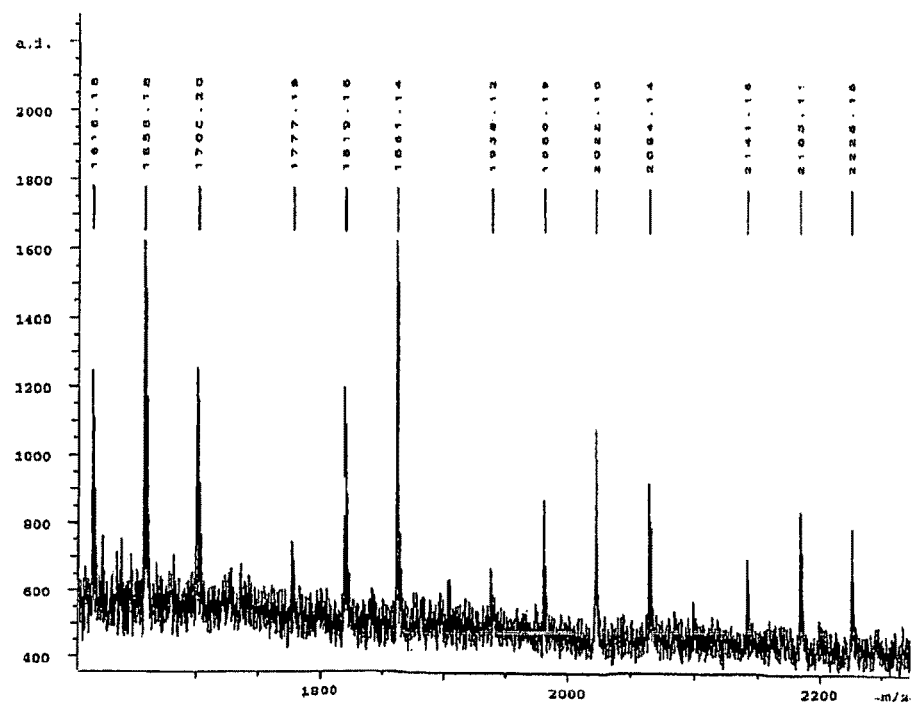
Figure 10:
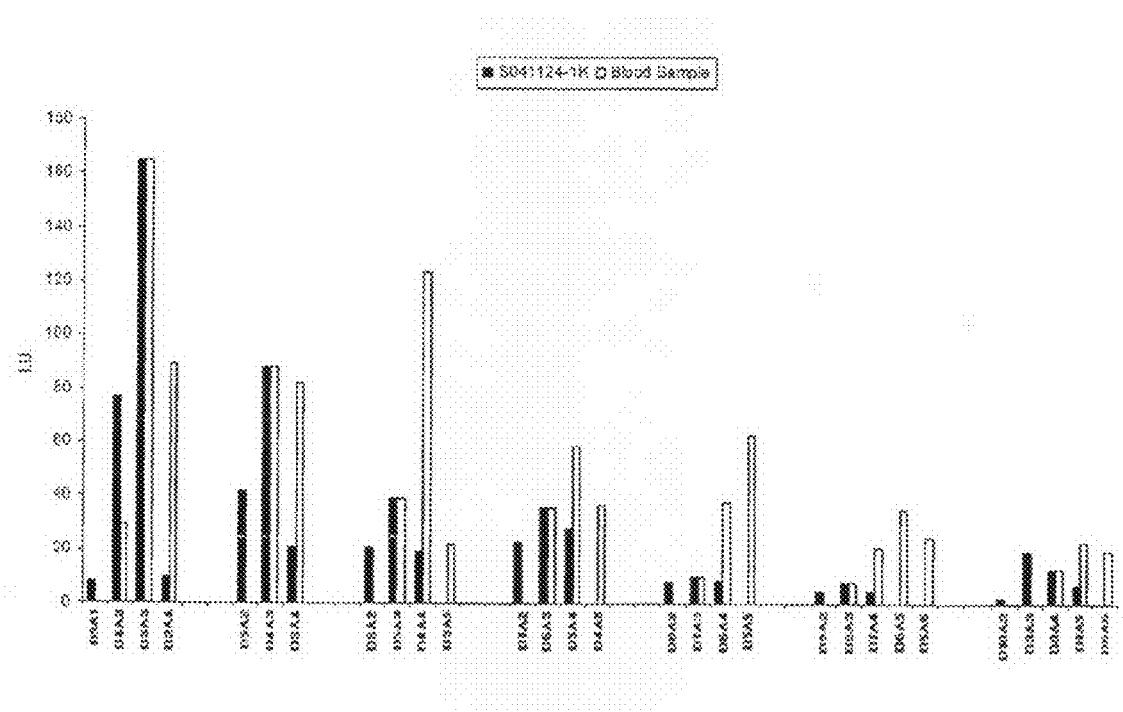

The MALDI-TOF MS revealed oligomers from DP2 to DP12 (FIG. 9). FIG. 10 compares the relative mass spectrometric signal intensities of oligomers and homologues of the native sample consumed to the post 3 weeks blood sample. A clear shift to higher acetylated homologues (higher $F_A$ values) in the blood sample is observed compared to the original mixture. Traces of homologues up to DP15 were found in the post 3 weeks blood sample. Quantitative determination of homologues by various methods (see Table 4 and the Method chapter) revealed a total ChOS concentration of 0.19 mg/ml serum after 3 weeks of consumption.

Two weeks after stopping the consumption no chitooligomers are detected in the blood stream anymore.

It is concluded that the T-ChOS compositions tend to be more bio available compared to hetero oligomer compositions comprising different compositions, such as $F_A$ values. In turn, this supports the conclusion that T-ChOS compositions comprise higher therapeutic activity compared to other hetero oligomer compositions.

Example 4

T-ChOS Homologues as Blockers for Chitinase-A Activity; A Model for Biostability of the T-ChOS Compositions Material and Methods Chitooligosaccharides (ChOS) (lots No. G020418 and G020218) were fractionated into homologue fractions, either by cation exchange chromatography or gel permeation chromatography or by the combination of both methods. The products were freeze dried and analysed for structure and sequence by MALDI-TOF mass spectrometry. Three other un-fractionated ChOS lots from Genis were also analysed by

TABLE 4

Absolute masses of fractons, oligomers and homologues found in a blood smple collected after 3 weeks of ChOS consumption. Masses were calculated according to relative GPC peak areas and relative MS signal intensities for a total mass of 1.34 mg per 7.0 ml blood

| | 1 | | 2 | | 3: Quantitative Determination of ChOS by GPC, HPIEC and MALDITOF | | | | |
|---|---|---|---|---|---|---|---|---|---|
| GPC Fraction | Mass est. [µg] | 1 Conc. [µg/ml] | Mass wt. [µg] | 2 Conc. [µg/mL] | GPC Fraction | Mass wt. [µg] | Conc [µg/mL] | HPIEC Homologue | Mass calc [µg] | Conc [µg/mL] |
| 1 | 150 | 21 | 130 | 19 | 2 | 270 | 39 | A2 | 270 | 39 |
| 2 | 160 | 23 | 150 | 21 | 3 | 110 | 15 | D1A2 | 80 | 11 |
| 3 | 190 | 27 | 180 | 26 | | | | A3 | 30 | 4 |
| 4 | 110 | 16 | 100 | 14 | 4 | 230 | 33 | D2A2 | 120 | 17 |
| 5 | 130 | 19 | 120 | 17 | | | | D1A3 | 110 | 16 |
| 6 | 120 | 17 | 120 | 17 | 5 | 100 | 14 | D3A2 | 10 | 1 |
| 7 | 90 | 13 | 100 | 14 | | | | D2A3 | 90 | 13 |
| 8 | 90 | 13 | 100 | 14 | 6 | 280 | 40 | D4A2 | 30 | 4 |
| 9 | 30 | 4 | 70 | 10 | | | | D3A3 | 200 | 29 |
| 10 | 270 | 39 | 570 | 81 | | | | D2A4 | 50 | 7 |
| | | | | | 7 | 180 | 26 | D5A2 | 10 | 1 |
| | | | | | | | | D4A3 | 80 | 11 |
| | | | | | | | | D3A4 | 90 | 13 |
| | | | | | 8 | 70 | 10 | D5A3 | 30 | 4 |
| | | | | | | | | D4A4 | 40 | 6 |
| | | | | | 9 | 20 | 3 | D6A3 | 10 | 1 |
| | | | | | | | | D5A4 | 10 | 1 |

1 Homologue determination by MALDITOF MS
2 Quantitative Determination of ChOS by GPC and MALDITOF MS Conclusions The consumption of 1.8 g ChOS daily leads to an absorption of these sugars into the blood stream. Traces of DP2 and DP3 oligomers are apparent in 1 week of consumption. An 84% of maximum uptake is reached in 2 weeks and maximum plateau of ChOS (100%) is reached 3 weeks after the onset of consumption. The overall maximum concentration was ca.190 µg per ml of blood, indicating 53% maximum absorption yield of daily administration (5 L blood volume). Oligomers of DP2-7 are found with (rather equal) concentrations of 14-40 µg per ml blood. Oligomers of DP8-9 are found in lower concentrations of 3-10 µg/ml. Oligomers up to DP15 were found in the blood. A comparison of the homologues found in the native sample consumed and in the blood reveals that homologues of higher degree of acetylation are preferably penetrating into the blood stream.

the same MALDI-TOF method (lots No. G040823, G050421 and G050421UF; where UF stands for ultrafiltrated through 1 kDa membrane to reduce the content of DP≤5).

Ultrafiltration was carried out on batch G050421, prepared by hydrolysis of a partially deacetylated chitin lot, which was homogenously deacetylated. Briefly 16 g of the ChOS were dissolved in 180 ml distilled water and diafiltrated on a 1 kDa regenerated cellulose membrane (Millipore, USA), using an Amicon cell. The final volume of the retained solution was 65 ml, yielding 0.582 g ChOS (Yield=33%). The total permeate volume was 970 ml. Both total permeate and final retentate were analysed by P4 Biogel chromatography and MALDI-TOF mass spectrometry as described in Example 4 The final retentate was lyophilised and referred to as G050421UF.

A purified Chitinase A preparation from *S. marcescens* was used as a standard Family 18 chitinase, and 4-methylumbelliferyl-beta-D-N,N'-triacetylchitotrioside (4-MU-A3), a chitin tetramer (A4) analogue, was used as a standard chitinase substrate.

The standard Chitinase A solution was 0.5 nM (500 pM) in 0.1 mg/ml BSA, 50 mM phosphate buffer pH 7.4 (Chit-A sol.) and the substrate solution was 40 µM 4-MU-A3 in 50 mM phosphate buffer pH 7.4.

Different concentration of each pure ChOS homologue (usually 0, 25, 50, 100, 200, 400 and 800 µM) was made in the substrate buffer. For the assay, 25 µl of the Chit-A solution was mixed with 25 µl of the substrate/blocking solution, incubated at 37° C. for 10 min. The reaction was stopped with 1.95 ml 0.2 M sodium bicarbonate buffer ($Na_2CO_3$). The formation of the product, 4-Methylumbelliferone (4-MU) was read for each reaction in a Perken-Elmer LS SOB Fluorometer. The excitation wavelength was 380 nm (5 nm adjusting slit) and the emission wavelength was 460 nm (4 nm adjusting slit). Each reaction was read in triplicate. To estimate blocking, 50% inhibitory concentration (IC50) was calculated for each ChOS homologue, using non-linear fit, $f=y0+a*exp(-b*x)$, where x equals specific activity of the chitinase and f equals oligosaccharide concentration (µM). Affinity of each homologue was calculated as inverted IC50. The formula used was $1/IC50*1000$.

Results and Conclusion

Even tough the chitinase A has an optimal activity at pH 5.5, the pH for the blocking experiments was adjusted at pH 7.4. This was done in order to free the amine groups of ChOS from protons, since earlier pilot experiments performed at pH 5.5 indicated low blocking activities of the ChOS homologues. Also this pH better resembles the physiological pH of blood and other physiological fluids, better reflecting the behaviour of the oligosaccharides in the human body.

Figure 11:
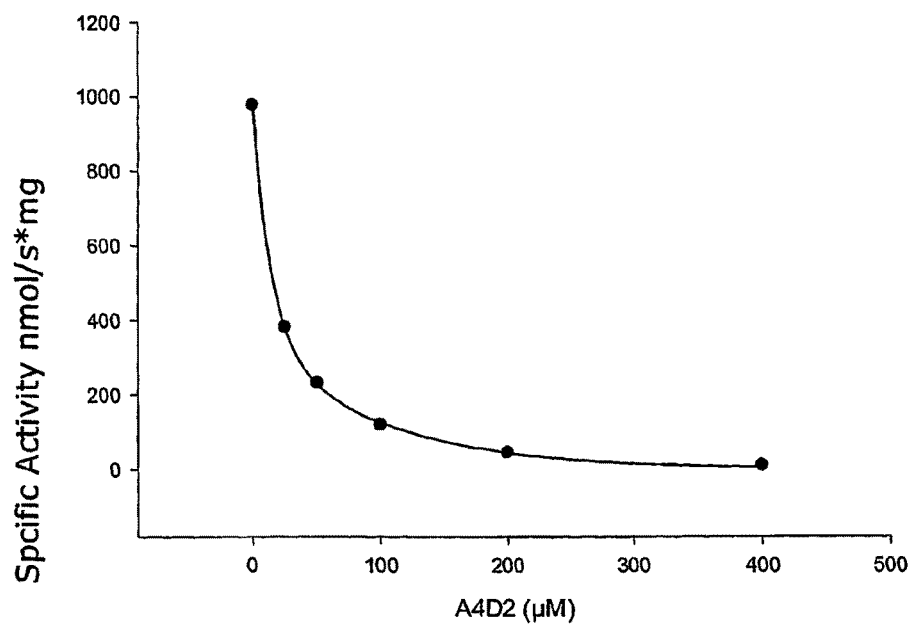
Figure 12:
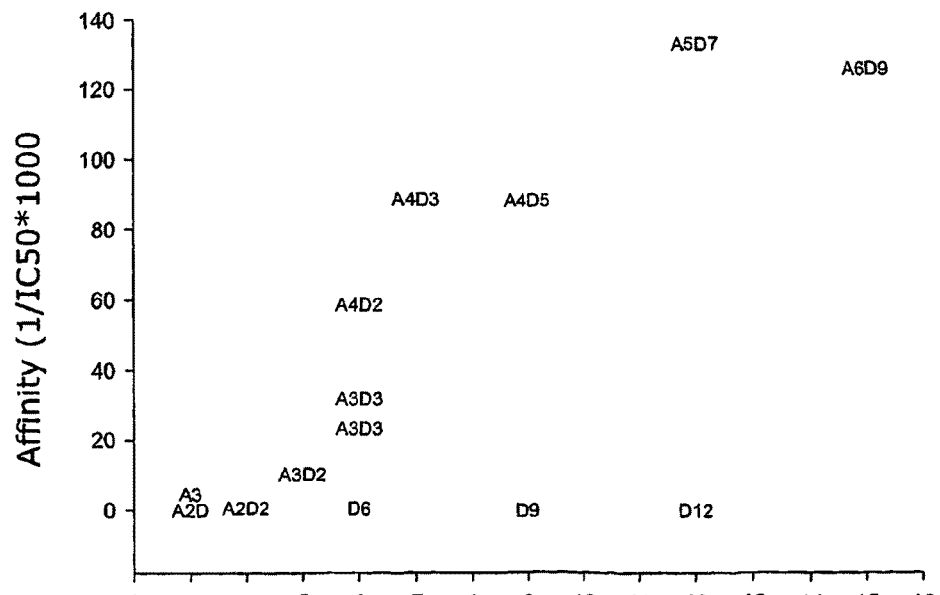
Figure 13:
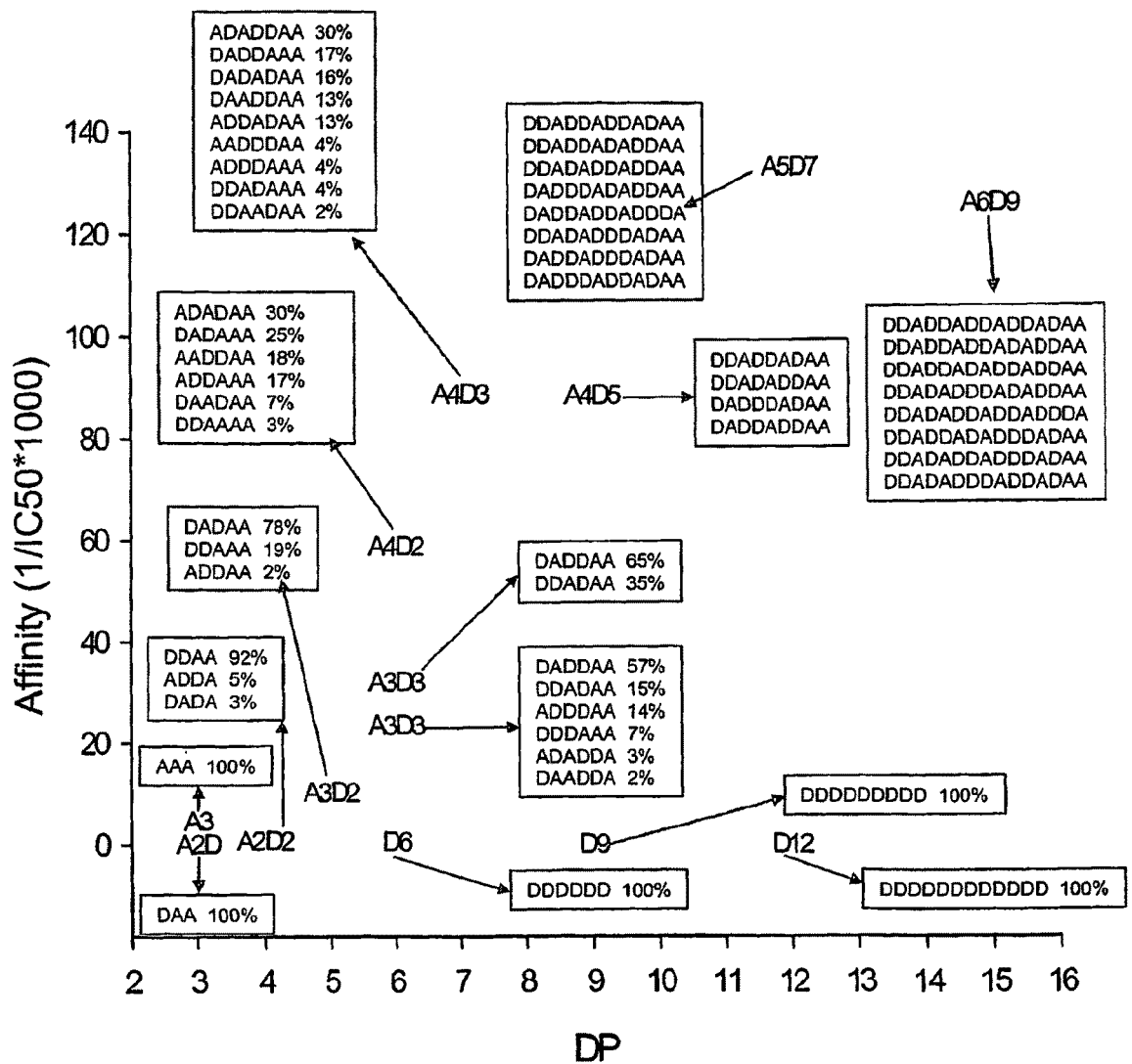

FIG. 11 shows typical ChOS blocking of the chitinase activity. The resulting IC50 was calculated 17 µM for the A4D2 homologue. Table 5 summarises the DP, homologue, the IC50, the calculated affinity and the sequences for all homologues tested. FIG. 12 shows the calculated affinity of each homologue tested. FIG. 13 shows the same as FIG. 12 as well as all sequences (isobars) comprising each homologue. Considering the blocking activity of different homologues two main rules can be drawn. The blocking is stronger as the DP is increased and at the same time the more acetylated homologues (more A units per molecule) show higher affinity. Therefore D6, D9 and D12 are all poor blockers. A4D2, A4D3, A5D7 and A6D9 (DP 6-12) showed the strongest blocking. These homologues can therefore be considered to possess the highest bioactivity due to their apparent affinity to the chitinase active side. DP12 (A5D7) shows the highest affinity and at DP15 (A5D7) the affinity is not significantly increased (FIGS. 12 and 13). The homooligomer A6 was cleaved by the chitinase A into A3, A2 and A1 as judged by MALDI-TOF.

However, the Chitinase A did not cleave any of the hetero-oligomers tested under the assay conditions (pH 5.5 and pH 7.4), as judged by MALDI-TOF mass spectrometry, indicating good biostability of the homologues. The reason for this high biostability is the complete hydrolysis of the substrate, by a Family 18 chitinase during the production of the ChOS.

When the un-fractionated ChOS preparations were tested in the same enzyme system, the IC50 was 70 µg/ml for G040823 (FIG. 14), 105 µg/ml for G050421 and 67 µg/ml for the ultrafiltrated G050421UF. This demonstrates that the method can be used to evaluate blocking activity and biostability of homologues in ChOS mixtures and does not require fractionation into homologues prior to analysis. Therefore, this method can be used as an evaluation of the average blocking activity of a ChOS preparation comprising a mixture of different homologues of hetero chitooligosaccharides. Such an evaluation would give an indication of the average binding affinity to the active site of the enzyme and the average biostability of the comprised homologues.

TABLE 5

Degree of polymerisation (DP), homologues, inhibition concentration (IC50), calculated affinity (CA) and sequences of the chitooligosaccharides tested.

| DP | Homologue | IC50 | CA* | Sequences |
|---|---|---|---|---|
| 6 | D6 | 1980 | 0.5 | DDDDDD 100% |
| 9 | D9 | NB* | 0 | DDDDDDDDD 100% |
| 12 | D12 | NB* | 0 | DDDDDDDDDDDD 100% |
| 3 | A2D | NB* | 0 | DAA 100% |
| 4 | A2D2 | 1387 | 0.7 | DDAA 92%, ADDA 5%, DADA 3% |
| 3 | A3 | 219 | 4.4 | AAA 100% |
| 5 | A3D2 | 96.7 | 10.3 | DADAA 78%, DDAAA 19%, ADDAA 2% |
| 6 | A3D3[1] | 31.3 | 31.9 | DADDAA 65%, DDADAA 35% |
|   | A3D3[2] | 42.7 | 23.4 | DADDAA 57%, DDADAA 15%, ADDDAA 14%, DDDAAA 7%, ADADDA 3%, DAADDA 2% |
| 6 | A4D2 | 17.0 | 58.8 | ADADAA 30%, DADAAA 25%, AADDAA 18%, ADDAAA 17%, DAADAA 7%, DDAAAA 3% |
| 7 | A4D3 | 11.2 | 88.9 | ADADDAA 30%, DADDAAA 17%, DADADAA 16%, DAADDAA 13%, ADDADAA 13%, AADDDAA 4%, ADDDAAA 4%, DDADAAA 4%, DDAADAA 2% |
| 9 | A4D5 | 11.3 | 88.5 | DDADDADAA, DDADADDAA, DADDDADAA, DADDADDAA |
| 12 | A5D7 | 7.5 | 133.0 | DDADDADDADAA, DDADDADADDAA, DDADADADDAA, DADDDADADDAA, DADDADDADDDA, DDADADDDADAA, DADDADDDADAA, DADDDADDADAA |
| 15 | A6D9 | 8.0 | 125.8 | DDADDADDADDADAA, DDADDADDADADDAA, DDADDADADDADDAA, DDADADDDADADDAA, DDADADDADDADDDA, DDADDDADADDDADAA, DDADADDADDDADAA, DDADADDDADDDADAA |

*CA = calculated affinity, 1/IC50*1000
*NB = no blocking found
A3D3[1] from G020418
A3D3[2] from G020218

Figure Legends

FIG. 11. The blocking effect of homologue A4D2 on Chitinase A. Non-linear fit, f=y0+a*exp(-b*x) is indicated. The 50% inhibitory concentration (IC50) for A4D2 was calculated as 17 µM.

FIG. 12. Calculated affinity of the homologues. The figure shows the affinity of each homologue tested (based on data in Table 5).

FIG. 13. Bioactivity and biostability of CHOS homologues as in FIG. 12 with sequences, see Table 5 for details.

Figure 14:
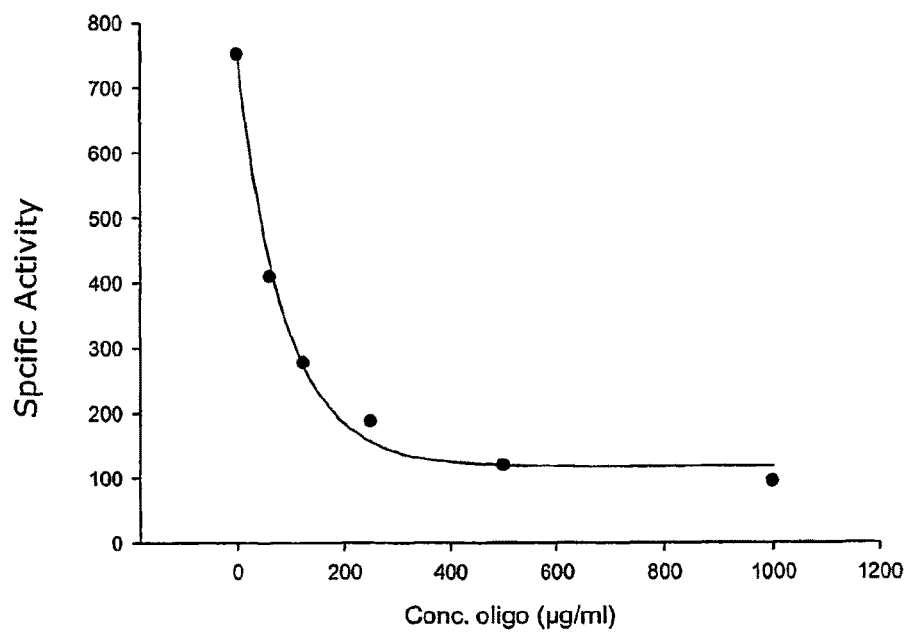

FIG. 14. The blocking effect of ChOS lot G040823 on Chitinase A. The IC50 was calculated as 70 µg/ml.

Example 5

Binding of Heterooligosaccharides to the 39-kDa Human Cartilage Glycoprotein (HC gp-39)

As HC gp-39 is a chitinase-derived protein, chitin oligomers (besides the polymer chitin) show the strongest affinities to this protein. On the other hand, chitin oligomers are rapidly cleaved by active Family 18 chitinases that are also found in the human body. Heterochitooligosaccharides (composed of A and D units) such as the T-ChOS compositions, possess a significantly higher biostability than chitin oligomers (only A units or homooligosaccharides). Thus, the objectives of the present work were to investigate how much the affinity of ChOS to HC gp-39 is influenced by the $F_A$ and moreover by the DP of heterooligosaccharides.

Materials and Methods

Qualitative and Quantitative Sequence Analysis of Heterochitooligosaccharides was performed as previously described (Example 4).

Affinity Studies

The affinities of non-covalent complexes between ChOS and HC gp-39 were analysed making use of the change of the intrinsic tryptophan fluorescence of the protein under binding conditions. The change of fluorescence intensity is caused by ligand-induced changes of the solvent cover of tryptophan residues and positively correlated with the sugar concentration.

HC gp-39 was dissolved in 25 mM Tris-HCl buffer pH 7.4 containing 1 mM dithiothreitol to a final concentration of 1.00 µM (protein solution). Different concentrations of homologues were prepared in 25 mM Tris-HCl buffer pH 7.4 containing 1 mM dithiothreitol (sugar solution). For each homologue 4 different concentrations were prepared: solution I 1.3-2.0 µM, solution II 6.5-16.0 µM, solution III 52.0-80.0 µM and solution IV 130.0-200.0 µM (the concentrations differed between the homologues). For the assay, 50 µl of the protein solution and 50 µl of each sugar solution (solutions I-IV) were preincubated separately at 25° C. In a thermoshaker for 15 min. Afterwards 50 µL of the thermostatted protein solution was mixed with 50 µL of the sugar solution (solutions I-IV in succession). The mixture was incubated for 7 min at 25° C. In a thermoshaker. The fluorescence was read for each reaction in a Perkin-Elmer LS 50B fluorescence spectrometer (Perkin-Elmer, Überlingen, Germany). The excitation wavelength was 295 nm (5 nm adjusting slit) and the emission wavelength 340 nm (10 nm adjusting slit) with a cut-off at 290 nm. Each reaction was measured in triplicate.

Calculation of Dissociation Constants

From the row fluorescence data the fluorescence of the blank was subtracted. F-F₀ was plotted versus the concentration of the homologue and the data were fitted by non-linear regression to a one-site saturation model employing SigmaPlot® software to obtain binding isotherms.

$$y=B_{max}*x/(K_d+x)$$

$B_{max}$: fluorescence intensity for a saturated binding domain of HC gp-39
$K_d$: dissociation constant.

Correlation between $K_d$ and $F_A$

The data of the dissociation constants for a series of DP6 homologues ($D_6$, $D_3A_3$, $D_2A_4$ and $A_6$) in dependence of the number of A units were fitted by non-linear regression (SigmaPlot® software) to a two-parameter hyperbolic decay.

$$y=a*b/(b+x)$$

Correlation between relative Affinities and $F_A$

The data of the dissociation constants were converted to relative affinities with 100% relative affinity for $A_6$ and 0% relative affinity for $D_6$. The relative affinities of $D_3A_3$ and $D_2A_4$ were calculated according to this virtual scale and plotted versus the number of A units. The data were fitted to a two-parameter single rectangular hyperbolic function by non-linear regression (SigmaPlot® software).

$$y=a*x/(b+x)$$

Results

Previous to the affinity studies, all ChOS used for the present work were analysed for purity and sequence composition. Chitin oligomer A6 (Seikagaku Co., Japan) was purified and amalysed before the affinity studies. All oligomers were checked for purity. Table 6 shows the sequence compositions of ChOS tested.

The affinities of complexes between ChOS and HC gp-39 were analysed using the intrinsic tryptophan fluorescence of the protein. The change of fluorescence intensity is depending on the sugar concentration and explained by a rearrangement of solvent molecules covering the surface of tryptophan under non-binding conditions.[24] The concentration-dependent fluorescence data were fitted by non-linear regression to a one-site saturation model (SigmaPlot® program, see FIG. 15). The dissociation constants found for $D_6$, $D_3A_3$ $D_2A_4$, $A_6$, and $D_5A_6$ were all in the µmolar range (FIG. 16).

As expected, the values for the dissociation constants are decreasing with increasing $F_A$ of ChOS. The decrease of the dissociation constants with increasing $F_A$ for the series of DP6 homologues ($D_6$, $D_3A_3$ $D_2A_4$ and $A_6$) is not a linear function. The data are best fitted to a hyperbolic decay function (y=a*b/(b+x); a: 419.932; b: 0.3839; $R^2$: 0.9986; FIG. 17). The inset in FIG. 17 shows the relative affinities [%] ($D_6$=0% and $A_6$=100%) with still 90.8% of the maximum affinity for $D_3A_3$.

The values of the dissociation constants are also decreasing with increasing DP and constant $F_A$ as the comparison of $D_3A_3$ ($F_A$ 0.5; $K_d$ 51.1 µM) and $D_5A_6$ ($F_A$ 0.55; $K_d$ 6.9 µM) shows. Interestingly, the $K_d$ values are even decreasing with increasing number of D units but constant number of A units as the comparison of $A_6$ (6 A units; $K_d$ 13.6 µM) and $D_5A_6$ (6 A units; $K_d$ 6.9 µM) shows (the $K_d$ of $D_5A_6$ is 14% of the $K_d$ for $D_3A_3$).

TABLE 6

Sequences/composition of CHOs employed for the binding studies on HG gp-39.

| Oligome- | Homologue | Sequences/Composition [mol-%] |
|---|---|---|
| 6 | D6 | DDDDDD 100% |
| 6 | D3A3 | DDADAA 49% DADDAA 51% |

TABLE 6-continued

Sequences/composition of CHOs employed for the binding studies on HG gp-39.

| Oligome- | Homologue | Sequences/Composition [mol-%] |
|---|---|---|
| 6 | D2A4 | ADADAA  30% DADAAA 25% |
|   |      | AADDAA  18% ADDAAA 17% |
|   |      | DAADAA   7% |
|   |      | DDAAAA   3% |
| 6 | A6 | AAAAAA 100% |
| 11 | D5A6 | * |

*sequences/composition not determinated

Conclusions

ChOS bind to HC gp-39 with affinity in the μmolar range (dissociation constants). The affinity Increases with increasing $F_A$ and DP even with increasing number of D units but constant number of A units. For the series of DP 6 homologues a 50% decrease of $F_A$ ($A_6 \square D_3 A_3$) causes only 9.2% decrease of affinity. Thus, ChOS of $F_A$ 0.5 to 0.75 are the optimal binding partners of HC gp-39 in the human body. They recover 90+% of the maximum binding capacity and contain enough D units (and thus D-D, D-A, A-D bonds) to show a significantly increased biostability in the human body. These compositions provide optimal therapeutic activity and are therefore herein referred to as therapeutic chitooligosaccharides (T-ChOS)

Figure Legends

Figure 15:
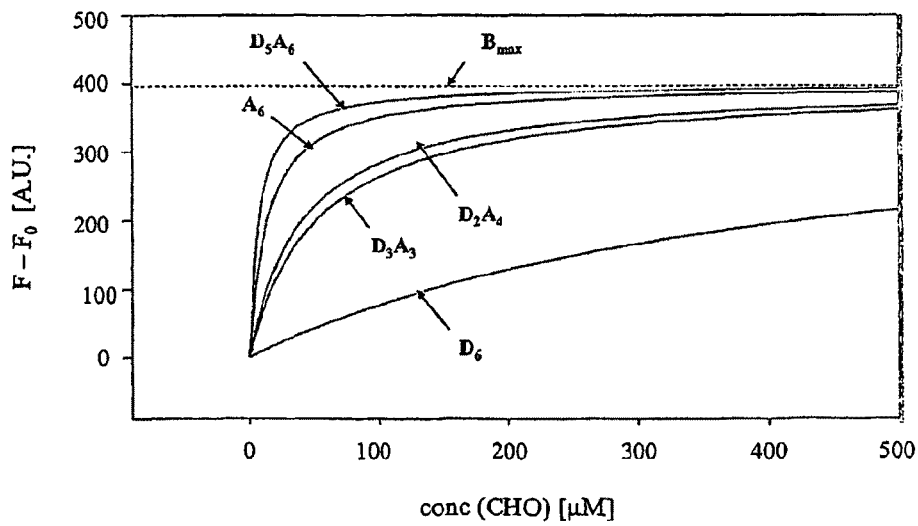

FIG. 15. Binding isotherms for D6, D3A3, D2A4, A6 and D5A6 binding to HC gp-39 with Bmax, the relative fluorescence intensity for binding site saturation.

FIG. 16. Dissociation constants for CHOs binding to HC gp-39 (logarithmic scale for Kd) In dependence of the FA of the homolog/oligomer. Dashed lines connect data points of DP6 homologs.

FIG. 17. Dissociation constants of DP6 homologues as a function of FA (number of A units). The data were fitted to a hyperbolic decay by non-linear regression. The inset shows the plot of relative affinities of DP6 homologues vs. The number of A units.

Example 6

The Effect of the Degree of Deacetylation in Chitobiomer Ingredient on Properties of a Calcium Phosphate—Chitobiomer Composite The Chitobiomer/calcium phosphate composite was prepared by mixing the solid fraction (containing 5% Chitobiomer or chitosan (80% DD), calcium phosphate and minerals) with corresponding amount of acidic medium. Table 7 summarizes the tested compositions in this Example. The feature of the paste after mixing was spongy and elastic and the setting time was significantly decreased as the DD was increased. The mechanical strength was also significantly Increased with increased DD (40% DD<<70% DD<80% DD).

Figure 18:
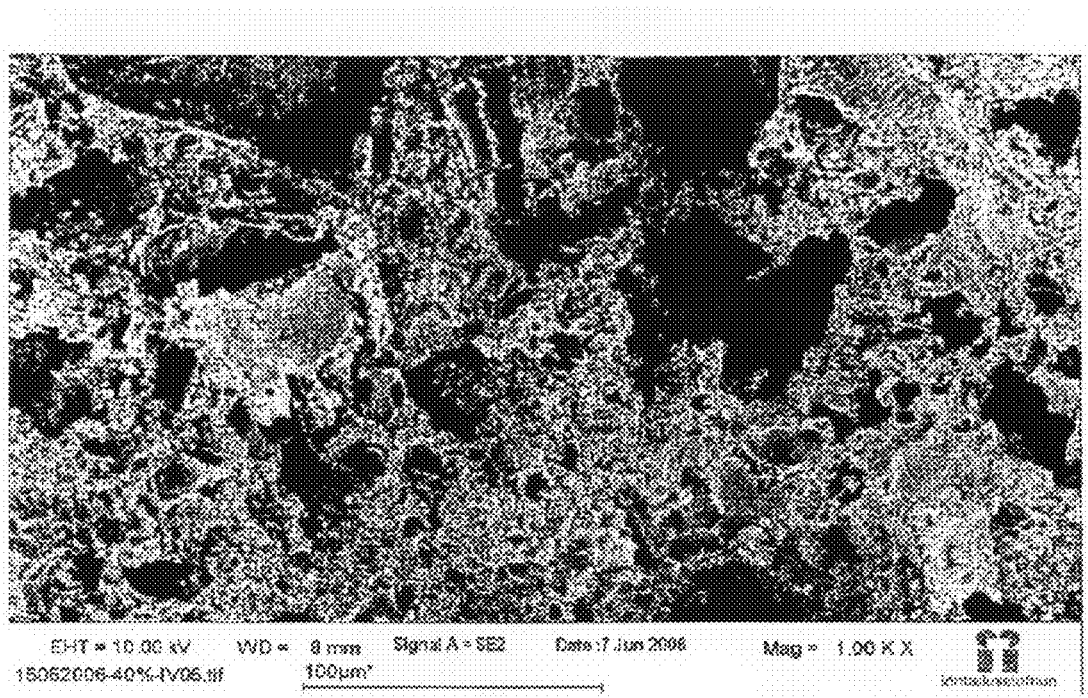

As shown in FIG. 18, the fracture surface is porous and macropores (pores of diameter larger than 50 μm) are abundantly found in the composite.

Figure 19:
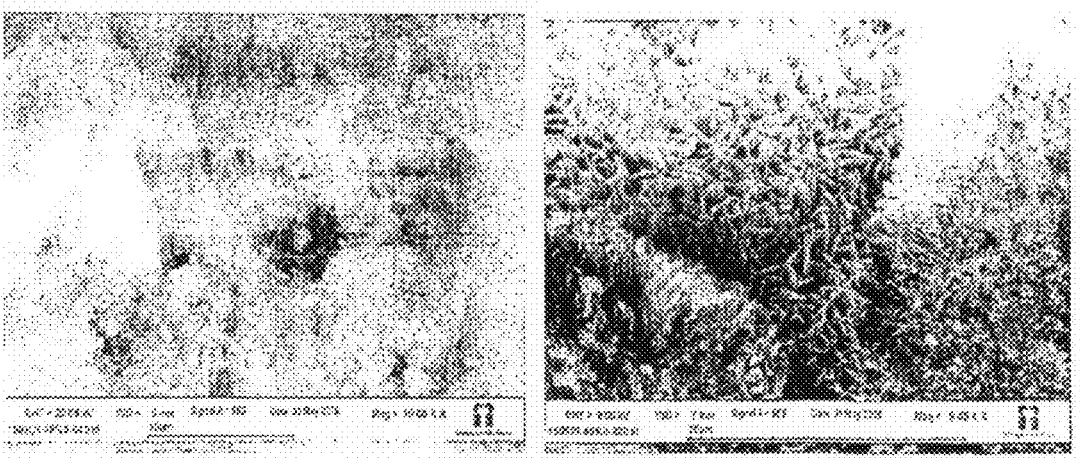

Different types (or sizes) of crystals were observed in composites prepared by polymers of different degree of deacetylation (FIG. 19). The composite with partially deacetylated chitin (40% DD) was dominated with rod-like crystals or particles (FIG. 20(a)), while the composite with 80% DD chitosan (FIG. 20(c)) was densely packed with plate-like crystals. For the preparation with 70% DD Chitobiomer (FIG. 20(b)), its crystal was the intermediate of 40% DD Chitobiomer and 80% DD chitosan composites, which contains both rod-like and plate-like crystals. This demonstrates that the degree of deacetylation of chitosan is affecting the crystal formation in the composite and there is an apparent shift from rod to plate structures at 70% DD. This difference may relate to the higher water binding capacity of the 40-70% DD Chitobiomers, compared to chitosan (80% DD). This affects the water availability and thus affects the crystal development in the composite.

The difference in crystal formation in the composite is particularly important since this may affect the strength of the composite and its biodegradability.

This example shows how the strength of the composite can be manipulated by the degree of deacetylation of Chitobiomer or chitosan. This can be used to control the biodegradability of the composite scaffold and thereby the access of migratory cells like macrophages and osteoclasts to penetrate the composite and thereby creating pores for penetration of cartilage and bone progenitor cells as well as epithelial cells creating vascularization necessary for bone development.

TABLE 7

Formulation of the three chitosan/calcium phosphate composites tested.

| | Composition with 80% DD | Composition with 70% DD | | Composition with 40% DD | |
|---|---|---|---|---|---|
| Solid Component | | | | | |
| Tetracalcium Phosphate | 1.08 | 1.08 | | 1.08 | |
| α-Tricalcium Phosphate | 0.84 | 0.84 | | 0.84 | |
| Sodium Glycerolphosphate | 0.26 | 0.26 | | 0.26 | |
| Chitosan (80% DD) | 0.23 | PDC (70% DD) | 0.23 | PDC (40% DD) | 0.24 |
| Subtotal | 2.41 | 2.41 | | 2.42 | |
| Liquid Component (84.6% water, 2.4% Ca(OH)$_2$ and 13% H$_3$PO$_4$) | 2.16 | 2.16 | | 2.40 | |
| TOTAL | 4.57 | 4.57 | | 4.82 | |

Figure Legends

FIG. 18. The fracture surface of the chitosan/calcium phosphate composite containing 5% Chitobiomer (40% DD). SEM pictures were taken after incubation at 37° C. for 7 days. Magnification 1000×.

FIG. 19. The effect of DD on crystal formation. SEM pictures were taken after incubation at 37° C. for 7 days. (a) Chitobiomer (40% DD), Magnification 10 KX and (b) 80% DD chitosan, Magnification 9.43 KX.

Figure 20:
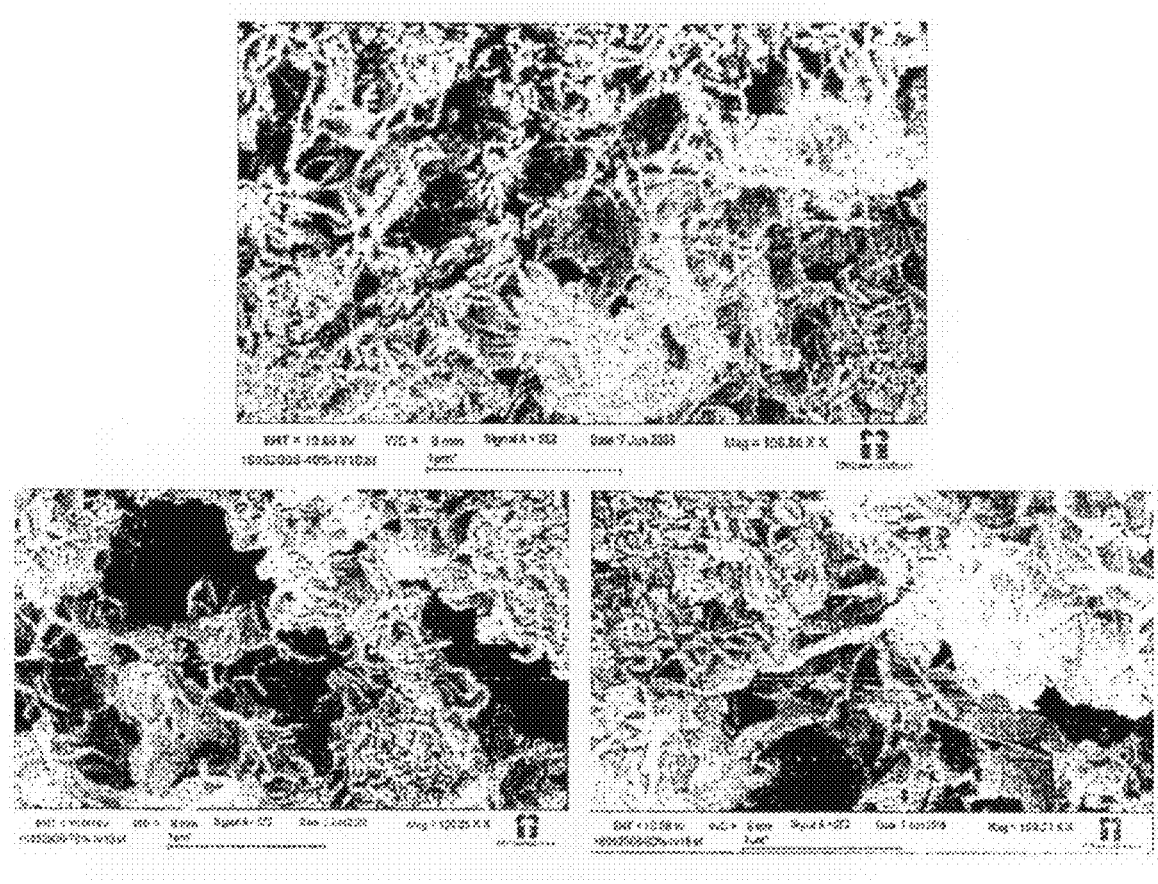

FIG. 20. SEM analysis of composites incubated at 37° C. for 7 days. (a) Chitobiomer 40% DD, (b) Chitobiomer 70% DD, and (c) chitosan 80% DD. Magnification 100 KX.

Example 7

Bone Healing Through Endochondral Ossification in Rat Femur 80 female rats were used to check the effect of a composite of 5% Chitobiomer with calcium phosphates (CAP). The entire group of animals was divided into 3 subgroups: I. Control (non-treated); II treated with calcium phosphates; and III treated with CAP containing 5% Chitobiomer. Chitobiomer and CAP were mixed together in the operation room and brought into a doughy consistency.

All the animals were anesthetized and their femurs were exposed at mid-shaft.

A 2-mm drill was used via compressed air, in order to perform a unicortical drill hole. The drill penetrated into the marrow space and the fresh hole was filled with either CAP alone or with CAP containing 5% Chitobiomer. In one group of rats, the holes were left as such, while the local bleeding was controlled in all animals. The muscles and the overlying skin were sutured by layers and the animals were allowed to move freely in their individual cages. In some animals the local injury was intentionally expanded by penetrating both cortices (through and through) and by widening the original diameter of the penetration site up to 5 mm. These cases were considered to undergo large-bony defects in comparison to the other groups of animals where the bone holes were well confined with no damage to the opposing cortical bone at the site of injury.

The three subgroups mentioned above were further divided and were sacrificed after 2, 3, 4 and 5 weeks postoperatively. Upon sacrifice all specimens were examined macroscopically and thereafter processed for microscopical examinations.

Results

Group I: Control Non-Treated Animals (Solitary Hole).

Figure 21:
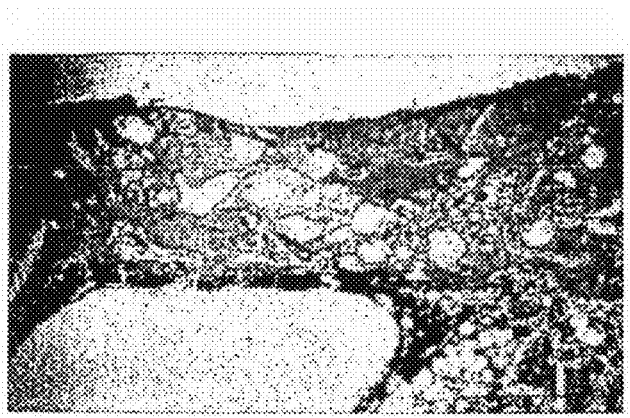

By 2 weeks, the openings of the bony holes contained Islands of irregular particles of new bone, yet the hole was not well sealed off from the adjacent tissues outside the bone. Also, new bone marrow tissue was apparent within the injured area. By 3 weeks, a thin layer of bone was noted bridging the bony hole. Almost no new trabecular bone was evident at the site of injury. By 4 weeks, the pattern observed above became even more evident. The new bony bridge appeared brittle as well as the new trabecular bone underneath it (FIG. 21). Substantial cracks were noticed in the original cortex of the femur at the site of the surgery. By 5 weeks, the new bony bridge sealing off the bony hole appears still as a fragile tissue, no bone marrow was evident whereas the cortical bone revealed multiple empty lacunae indicative of osteocytic damage and death.

Group II: CAP-Treated Animals (Solitary Hole)

Figure 22:

By 2 weeks, the tissue response was limited to the site of the bone injury and expressed itself in the production of a large number of new bone trabecules within the bone marrow space underneath the implanted paste of CAP. A large mass of CAP was noted at the site of its implantation—within the bony holes. No cellular response was noted outside the cortical borders, i.e., along the periosteum. By 3 weeks, the pattern of response was similar to that described above, although more bony tissue was involved in the "bridging" of the hole. By 4 weeks, the new bony bridge sealed off the injured marrow from the outside environment, appeared more organized and appeared as a continuous layer and healthy bone (FIG. 22). Further, underneath the site of the original hole newly developed marrow tissue was evident along with scattered bone trabecules. At that time interval, no remnants of the implanted CAP could be identified anymore. By 5 weeks, by and large, the pattern of development followed that noted in the previous 2 weeks. The re-establishment of a new bony bridge appeared complete and, thereby, Sealing off the recovering marrow tissue from the surrounding tissues. By that time a new marrow tissue was obvious whereas the bone trabecules within the marrow space showed multiple cracks within them.

Group III: Chitobiomer CAP-Treated Animals (Solitary Hole)

Figure 23:
Figure 24:
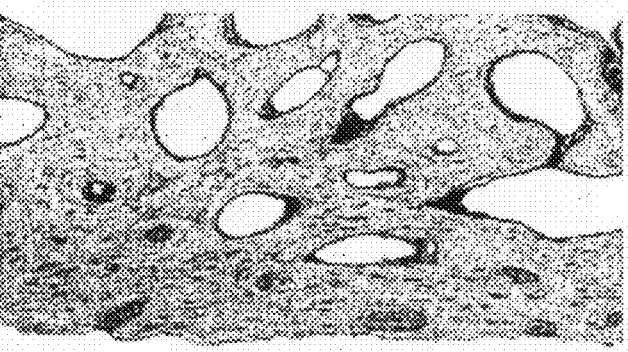

By 2 weeks, the site of injury revealed clear signs of tissue reaction in the form of new cartilage and bone formation along with new bone marrow tissue (FIG. 23). The penetration site was already completely closed. A unique feature noted at that time interval was the marked response of the original marrow tissue which was occupied by a well-developed network of new bone trabecules. The latter were embedded within a rich tissue of marrow which was comprised of mononuclear cells, fat cells and blood capillaries; an additional unique feature related to the cellular response within the original cortical tissue. This was manifested by the appearance of multiple cells within the cortex itself—bone cells, connective tissues cells and capillaries. By 3 weeks, the bony bridging was completed. The bridge was composed of a new trabecular network that was connected to the original cortical bone on both sides of the drill hole. Within the marrow space the new bone trabecules were connected with the inner surface of the original cortex. A well-developed marrow tissue was evident. By 5 weeks, a solid bridge of trabecular bone was sealing completely the penetration site, and a new "girdle" of trabecular bone was surrounding the original cortex. Remnants of Chitobiomer were still seen at the site of the original implantation. FIG. 24 shows the histology of the new and healthy bone tissue at week 4 post op.

Large Bony Defect.

By 2 weeks, a larger defect (5-6 mm) induced in one cortex and treated with CP+Chitobiomer was examined. By that time the entire marrow space revealed a large mass of new trabecular bones which were continuous via the penetration hole with the new mass of bone trabecules at the outer surface of the cortex. Most of the original cortex was engulfed by a new layer of trabecular bone that was in direct communication with the outer surface of the cortex. In contrast to the woven bone noticed in a similar case that was treated with CAP alone, the new trabecules within the marrow space appeared more organized and more dense. The original cortical layer of the femur at that region revealed multiple lacunae Inhabiting the osteocytes. Capillaries including erythrocytes were also noted within the cortex. Another animal of the same experimental group (2 weeks, Chitobiomer, large defect) exhibited a large mass of cartilage outside the femur's outline. This feature could be the result of the inductive stimuli of Chitobiomer upon progenitor cells within the periosteum. The newly formed cartilage subsequently underwent mineralization and transformed into an active locus of endochondral ossification. The formation of new bone outside the femur was at areas so extensive that it ended up with the development of exostoses that were connected to the original femur.

By 3 weeks, we examined a case whereby the drill got through both cortices. Relatively large pieces of intact cortices were found as separate entitles farther away from the original bone. Undoubtedly one of the most prominent features observed were the large de novo masses of cartilage that originated and kept their attachment with the periosteum of both the detached pieces of cortex and the original femoral cortex. The newly formed cartilage kept its continuity with the new cartilaginous tissue within the marrow space. The new cartilage revealed all the stages of tissue differentiation characteristic to this tissue. Starting with cartilage progenitor cells then young chondroblasts then mature chondrocytes then hypertrophic chondrocytes then mineralization of the matrical substance followed by the ossification process, so characteristic to the endochondral type of ossification.

The entire process described above lasted for only 3 weeks which is indicative of the immense potential of Chitobiomer (5%) to induce new cartilage from progenitor cells both within the periosteum and the marrow tissue. It appears as if Chitobiomer possesses a strong osteoinductive potential especially in cases of more extended and complicated injuries; whereby the native processes are not capable of overcoming a critical injury via a process that will yield a genuine regeneration of the original tissue, namely bone; But rather enable only a healing process which ends up with a non-union.

Moreover, CAP which served as the carrier of Chitobiomer, by it self also failed to achieve what was noted in the Chitobiomer-treated specimens. CAP is a good osteoconductive material but lacks the inductive capacity that Chitobiomer possesses first on cartilage formation and subsequently on the latter's ossification.

In summary, in vivo experiments using the adult female as the model, Chitobiomer was found to possess osteoinductive properties that resemble to a great extent those of BMPs. Its targets are the genetically determined cells within the periosteum, endosteum and marrow tissue that upon the appropriate trigger differentiate into cartilage cells that eventually ossify. The concentration used in the present study: 5% appeared highly potential, a dose-response study is essential in order to determine the optimal percentage of Chitobiomer needed to obtain the above findings.

By using polarized light during microscopical observations of a bone section, the orientation of the collagen fibers (Type I collagen) were analyzed. In an intact bone these fibers have a regular orientation, whereas in a more "primitive" embryonic-type of bone this orientation is lacking. The figure shows, that the fibers have a regular orientation indicating that the bone formation taking place is following the endochondral ossification pathway. Macrophages were shown to invade the CAP-Chitobiomer composite resulting in a gradual degradation of the Chitobiomer as it is replaced by new cartilage and bone tissue.

Conclusions

In summary, in vivo experiments using the adult female rat as the model, Chitobiomer was found to possess osteoinductive properties that resemble to a great extent those of BMPs. The bone formation follows the endochondral ossification pathway as is demonstrated by the histology figures. The process of endochondral ossification is characterized by cartilage formation before bone formation. Cartilage formation does not require oxygen in contrast to the bone forming stage, so formation of new blood vessels is required before the transformation of cartilage into bone can take place.

Reaction to the Chitobiomer was characterized by a formation of new cartilage tissue within the Chitobiomer implant and an induction of a rich formation of new vascular tissue within the new cartilage, resulting in the new tissue replacing Chitobiomer and only remnants of Chitobiomer being detected in the implants. Furthermore, cartilage cells are formed near the remnants of Chitobiomer and mineralized cartilage is detected adjacent to newly formed bone tissue supporting that the new bone formation follows the endochondral ossification pathway. Chitobiomer possesses inductive properties upon osteogenic cells both in the marrow tissue as well as in the periosteum. The chondrocytes form cartilage, before bone formation takes place and the chondrocytes, at the osteoblast-chondrocyte boundary, undergo terminal differentiation into hypertrophic chondrocytes expressing Type II collagen and secrete angiogenic factors, which mineralizes the calcified cartilage.

Figure Legends

FIG. 21. Untreated animal at 4 weeks post operation. The image shows the side of the implant, a fragile tissue is bridging the bone gap and the status of the healing was characterized as non union.

FIG. 22. Calcium phosphate treated animal at 4 weeks post operation. The image shows the side of the implant, remnants of calcium phosphate crystals are embedded in the fragile tissue bridging the bone gap. The status of the healing was characterized as non union.

FIG. 23. Animal treated with calcium phosphate-Chitobiomer composite at 2 weeks post operation. The image shows the side of the implant, cortical bone is covering the bone gap with dense trabecular bone underneath the new cortex. The status of the healing was characterized as complete union.

FIG. 24. Animal treated with calcium phosphate-Chitobiomer composite at 4 weeks post op. The image shows healthy new trabecular bone.

Example 8

The Effect of T-ChOS in Rheumatoid Arthritis, Using the Type II Collagen Induced Arthritis Rat Model Materials and Methods.

Figure 25:
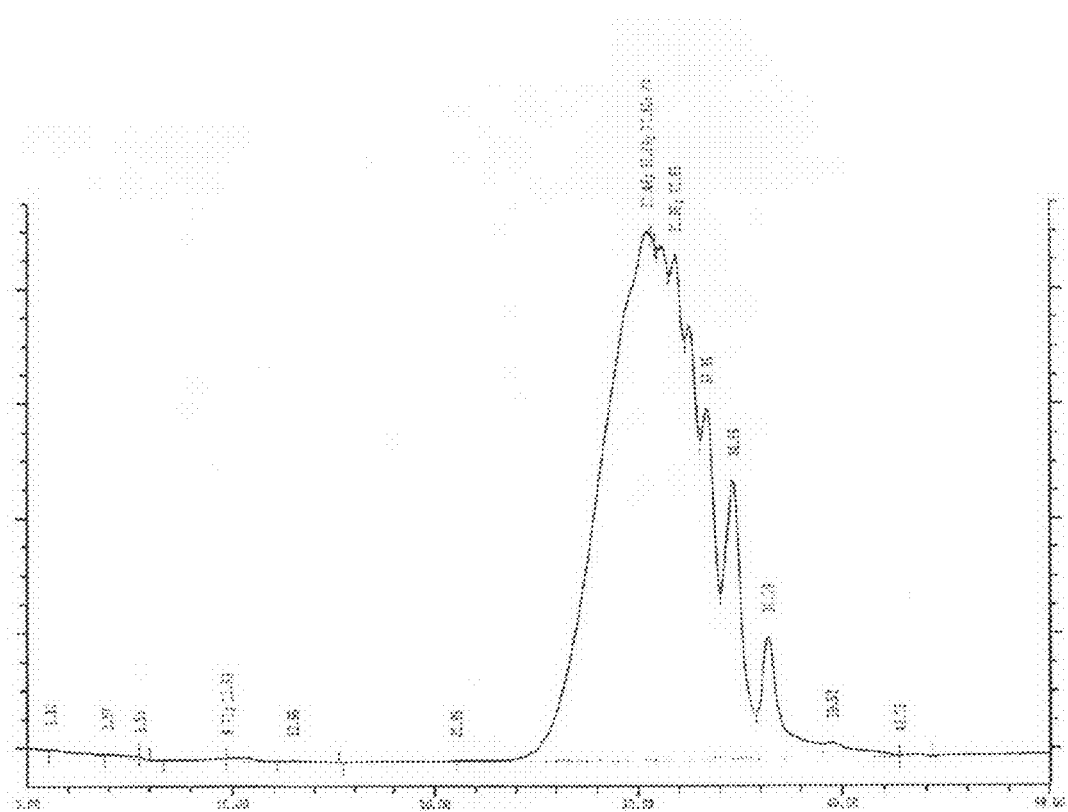

A preparation of chitooligomers composing ≥60% of T-ChOS compositions was produced by Genis, according to Example 2 (lot G051128), FIG. 25 shows the composition. Animal subjects in this study were female Lewis rats weighing 159-179 grams (mean 171 g) on day 0 of the study. Animals were identified by a distinct number at the base of the tall delineating group and animal number. After randomization, all cages were labeled with protocol number, group and animal numbers with appropriate color coding.

Animals (10/group for arthritis, 4/group for normal), housed 4-5/cage, were anesthetized with Isoflurane and injected with 300 µl of Freund's incomplete Adjuvant containing 2 mg/ml bovine type II collagen at the base of the tail and 2 sites on the back on days 0 and 6. T-ChOS treatment in the water was initiated on day 0 of the study and continued through day 17 with adjustments of concentration made on days 0, 6, 9-17, (weighing days).

Experimental groups are shown in Table 8

TABLE 8

Experimental design.

| Group | N | In Water Treatment Day 0-17 |
|---|---|---|
| 1 | 4 | Normal controls + water |
| 2 | 10 | Arthritis + water |
| 3 | 10 | Arthritis + 0.125 (3.57 mg/kg/day) |
| 4 | 10 | Arthritis + 0.25 (7.14 mg/kg/day) |
| 5 | 10 | Arthritis + 0.5 (14.29 mg/kg/day) |
| 6 | 10 | Arthritis + 1 (28.57 mg/kg/day) |
| 7 | 10 | Arthritis + 2 (57.14 mg/kg/day) |

The Table shows group no., number of individuals per group and the treatment of each group. Different doses are indicated in mg per kg rats per day.

The main parameter tested were the left and right ankle diameter of the hind paws of the rats, which was measured daily during the inflammation period. Other parameters of interest were histological scores measured in animals at day 17. Histological evaluation was performed in ankle and knee joints. The joints were cut in half longitudinally (ankles) or in the frontal plane (knees). Samples were preserved and decalcified (5% formic acid) and processed through graded alcohols and a clearing agent, infiltrated and embedded in paraffin, sectioned, and stained with Toluidine Blue. All tissues from all animals were examined microscopically and observations were entered into a computer-assisted data retrieval system.

Effect of T-ChOS on inflammation was analyzed applying ANOVA and t-tests (parametrical or non-parametrical tests) on the ankle diameter data.

Results

Figure 26:
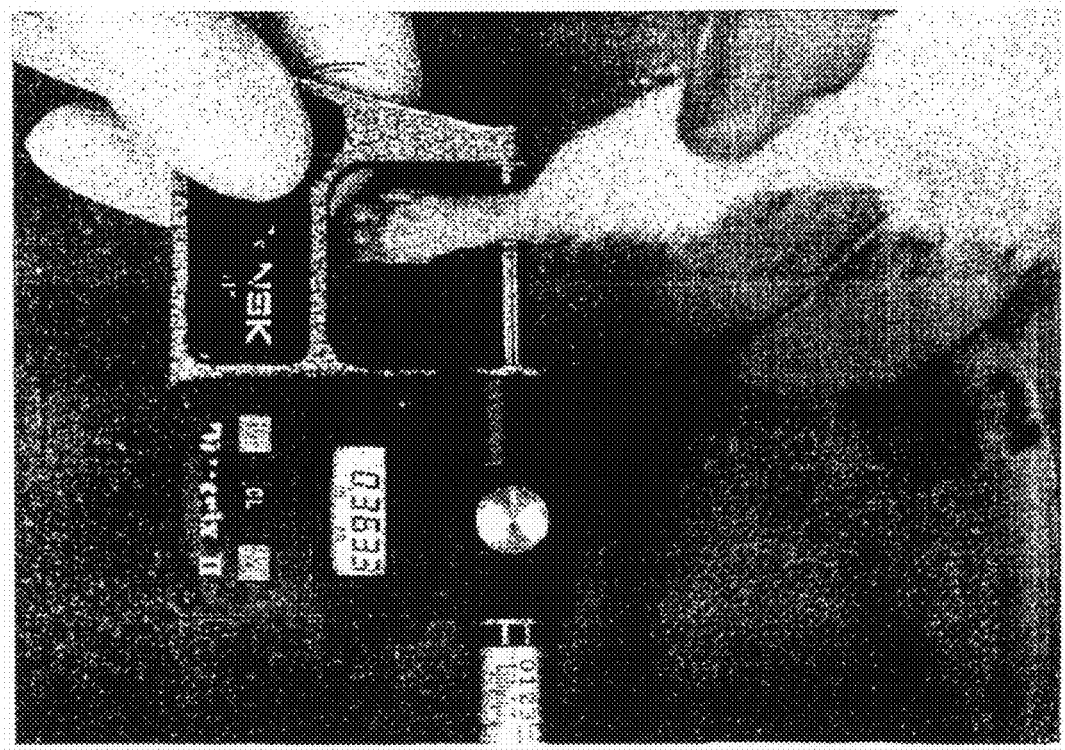
Figure 27:
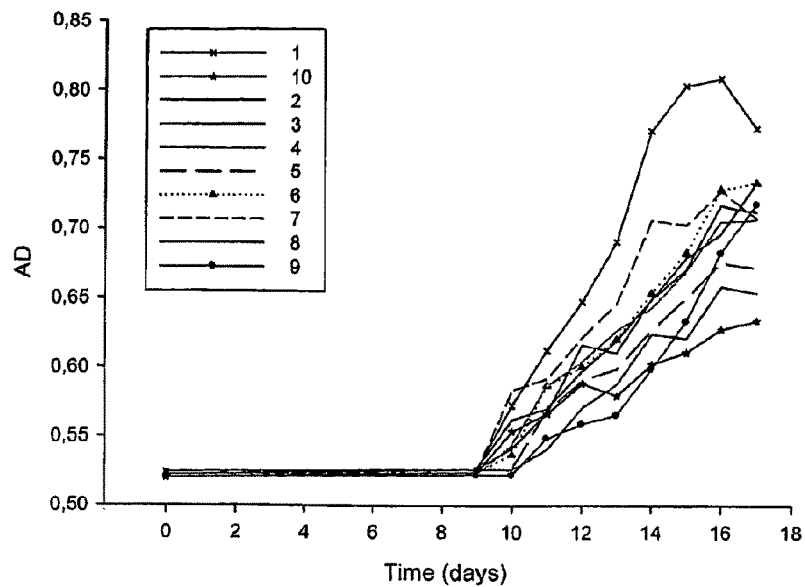

FIG. 26 shows the main method of monitoring the inflammation (the arthritis score). The ankle diameter for left and right ankle was measured daily from day 9. FIG. 27 indicates the RA score of collagen Injected rats without any other treatment. The inflammation is detected at day 10 and is gradually increased up to day 15-17.

Figure 28:
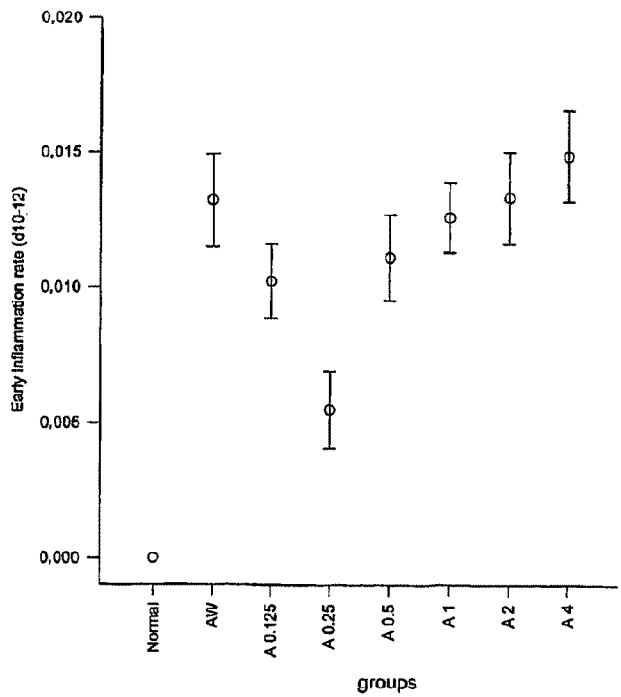

FIG. 28 shows the effect of different doses of T-ChOS on the early ankle inflammation rate (day 10-12). There is a clear dose depending effect from the AW group (0 dose) to the A 0.25 group where the reduction in inflammation rate was 58% and highly significant (p<0.01). Secondly, with higher dose the effect disappeared gradually.

Figure 29:
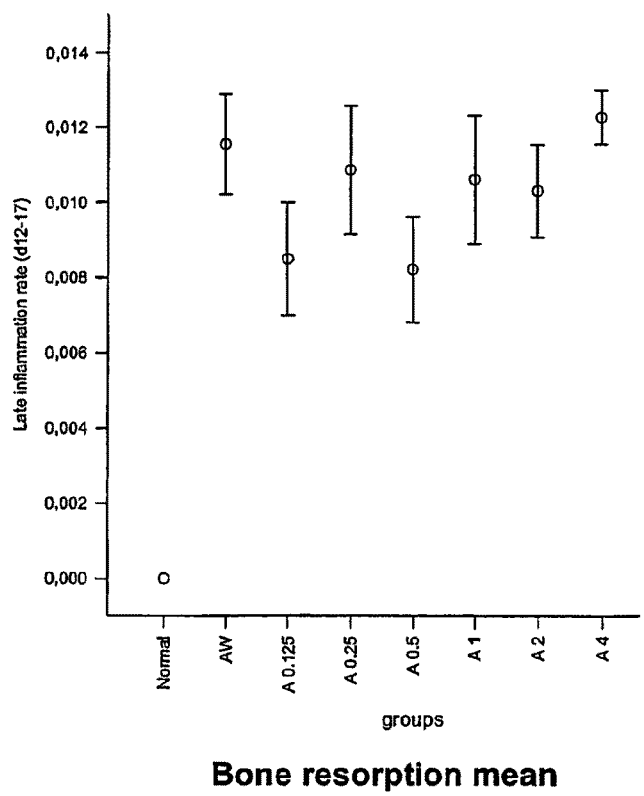

FIG. 29 indicates the effect of different doses of T-ChOS on the late ankle inflammation rate (day 12-17). The dose depending effect seen earlier has disappeared.

Analysis for the whole linear phase of the ankle inflammation (day 9-15) were also performed. The only group that showed a significant reduction in the inflammation rate of that period was the A 0.25 group where the effect was 28% (t-test; p<0.05, see Table 9).

Figure 30:
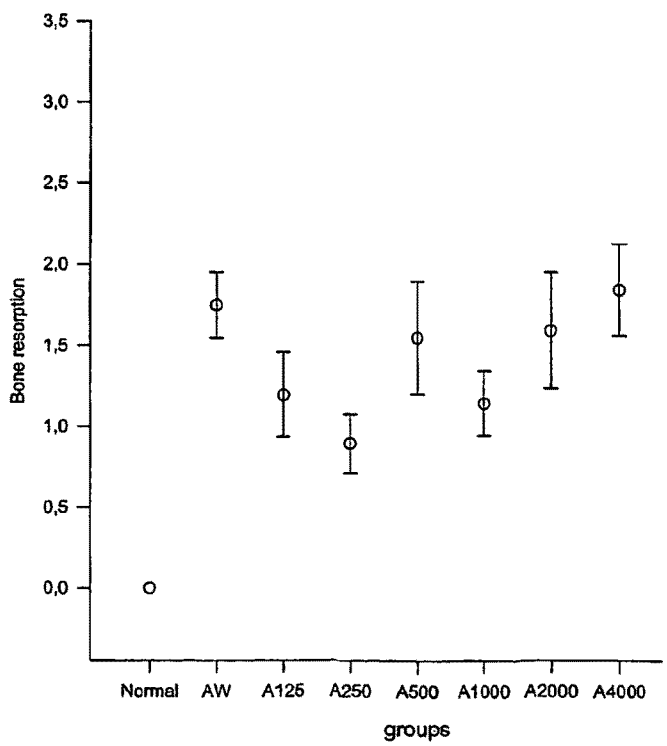

For histological inflammation and damage score from day 17, the main results are summarized in Table 9 for the most active groups. These were A 0.25. Bone resorption (the breakdown of bone tissue) was decreased 48% and this was the strongest effect on all the histological parameters. FIG. 30 shows the clear dose effect, but the A 0.5 group seems to be out of phase. There was a 28% significant reduction in inflammation and a 40% reduction in scar tissue formation (pannus) in the inflamed tissue. There was a 29% reduction in cartilage damage by T-ChOS but this effect—was not statistically significant. Finally, there was a significant reduction (33%) in histopathologic score but this factor was the sum of inflammation, pannus, cartilage damage and bone resorption scores for each rat.

TABLE 9

Summary of the main parameter tested in the study.

| Parameters examined | AW mean | A 0.25 mean | Reduction | A 0.25 vs AW |
|---|---|---|---|---|
| Inflammation rate (9-15 d) | 0.0124 | 0.00888 | 28% | * |
| Inflammation | 4.2 | 3.1 | 26% | * |
| Pannus | 1.75 | 1.05 | 40% | * |
| Cartilage Damage | 2.1 | 1.5 | 29% | 0 |
| Bone Resorption | 1.5 | 0.9 | 49% | ** |
| Histopathologic score | 9.8 | 6.55 | 33% | * |

The Table shows the means of the A 0.25 group compared to that of the AW (Arthritis and water) group, reduction of syntomps (%), statistical significance 0 = not signif, * = significant p < 0.05, ** = significant p < 0.01.

Conclusions

There was a strong significant effect of the T-ChOS in the early phase of the collagen type II induced arthritis in rats. The reduction in the inflammation rate of the ankles was at its best 58% in the early phase. This effect was dose related, showing the maximum effect in the A 0.25 group which is equivalent to 0.5 g daily dose in humans. But with higher doses the effect gradually disappeared. However, all histological scores, except one showed a significant reduction of arthritis conditions as a response to the optimum T-ChOS dose at the end of the experiment. Strongest effect was observed on reduction of bone degeneration (48%) and prevention of pannus (40%).

It was concluded that orally administered T-ChOS preparation significantly reduced tissue degeneration and reduced scar tissue formation in the inflamed joints. This supports other results indicating tissue regenerative activity of T-ChOS (Example 7) and reduction of fibroblast growth in tissue culture (Example 9).

Figure Legends

FIG. 25. HPLC analysis of the T-ChOS material tested, lot G051128. The Figure shows the relative quantities of sugars of different molecular weight, from DP2 to ca. 15.

FIG. 26. The measurement of ankle diameter as an indication of inflammation (arthritis score).

FIG. 27. The AD (ankle diameter) arthritis score. The ankle diameter (left+right ankle) in 10 individual rats Injected with collagen at day 0 (Group 2; arthritis+water).

FIG. 28. The effect of T-ChOS (all doses) in early ankle inflammation rate. (Early inflammation rate as average increase in left and right ankle diameter from day 10, 11 and 12). Means and standard errors are indicated.

FIG. 29. The effect of T-ChOS (all doses) in late ankle inflammation rate. (Early Inflammation rate as average increase in left and right ankle diameter from day 12-17). Means and standard errors are indicated.

FIG. 30. The effect of T-ChOS (all doses) In bone resorpsion as judged by histological examination. Means and standard errors are indicated.

Example 9

Inhibition of Fibroblast Proliferation by Immobilized T-ChOS

Materials and Method

Micro-Plate Coating:

Coating solutions for the micro-plate were prepared by dissolving gelatin (Bio-Rad, USA) in Hanks balanced salt solution (HBSS) at 37° C. to a concentration of 0.1%. Half of this solution was supplemented with T-ChOS to a final concentration of 1000 µg/ml and the other half served as a control. All solutions were sterilized by ultra filtration (0.22 µm Nalgene filters).

Microplate (96 wells Nunc, Denmark) was coated by adding 100 µl of the gelatin solutions into each well and Incubating at 4° C. over night. Excess solution was discarded and the plates stored with HBSS at 4° C.

Fibroblast Plating and Counting

Human fibroblasts were harvested by trypsination from confluent T-25 culture flask and seeded, at $1 \times 10^5$ cells/ml of RPMI 1640 medium with 10% serum, into the coated microplate wells. The cells were maintained at 37° C. and 5% $CO_2$ for three days and before the number of cells was determined by counting under a light microscope. Each experimental condition was repeated for eight wells.

Number of cells counted within a defined field in each of the eight wells (fibroblast density). The counting was done after one, two and three days in culture. Data was analyzed statistically (ANOVA).

Results

Figure 31:
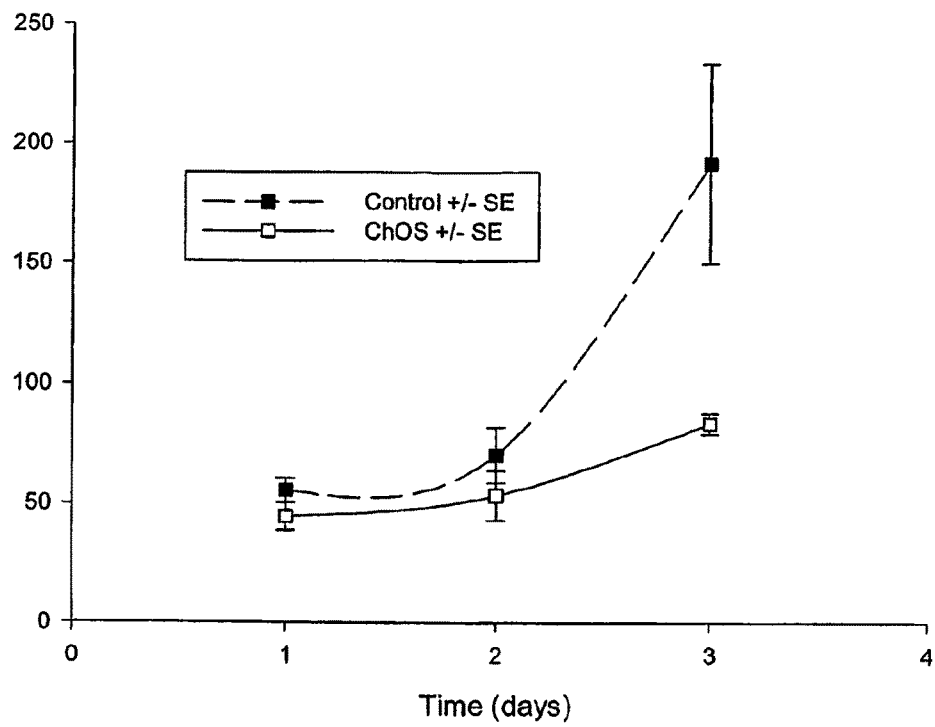
Figure 32:
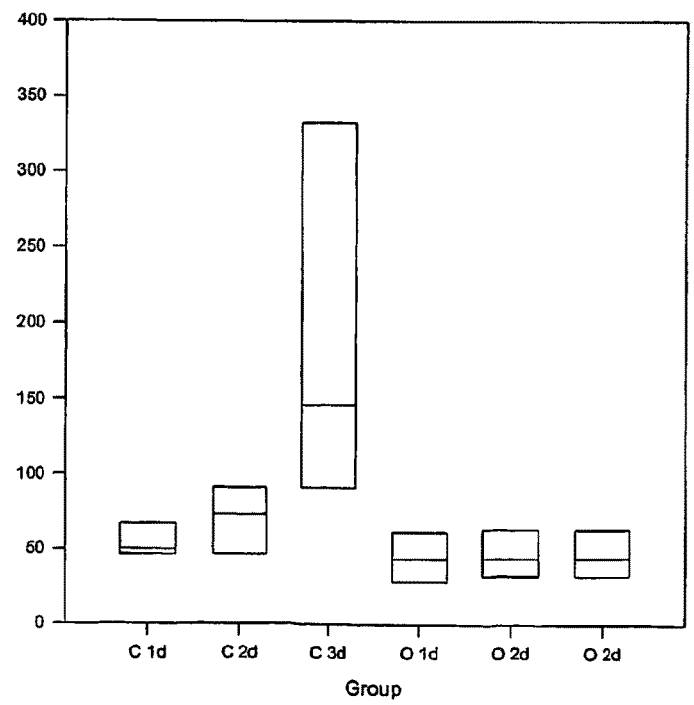

Statistical analysis revealed non-normal distribution of data. Therefore the tests ANOVA on Ranks, followed by Kruskal-Wallis One Way Analysis of Variance on Rank, were applied. This immobilized T-ChOS in gelatin halted significantly the growth of the fibroblasts, as shown in FIGS. 31 and 32.

Conclusion

In this experiment we were able to demonstrate that when the T-ChOS were imbedded into a gelatin coating in the culture plate, they were able to reduce significantly the proliferation of fibroblasts on the gelatin surface.

Together with scientific reports on effect of chitosan on wound healing, our earlier experience with Chitobiomers, both oligomers and polymers, and the current results; we conclude that the T-ChOS are able to suppress formation of fibrous tissue by fibroblasts, while promoting regeneration of the authentic tissues, such as bone, cartilage and other hard and soft tissues. This mechanism of wound healing is greatly advantageous, since it does not result in formation of scar tissue and preserves the integrity and functionality of the original tissue.

Figure Legends

FIG. 31. Fibroblast growth (density vs. time) on gelatin layer with and without 100 µg/ml Immobilized T-ChOS. Mean (n=7-8), +/−Standard error FIG. 32. Statistical evaluation of the effect of T-ChOS on the proliferation of fibroblasts during incubation of three days (d1-d3). C symbolizes untreated and O symbolizes treated cells.

The invention claimed is:

1. A dual component biomaterial composition comprising a solid component and a liquid component, for in situ crystallization of said composition, for enhancing bone regeneration and haemostasis in the healing of a fractured or severed bone in a mammal, said solid component comprising soluble partially deacetylated chitin with a degree of deacetylation (DD) between 30% and 60% and calcium phosphate,
said liquid component comprising an aqueous acidic medium, and
wherein the partially deacetylated chitin is prepared by a process comprising:
partially deacetylating chitin polymer with alkali treatment, wherein said alkali is cooled prior to mixing with the chitin, the deacetylation reaction maintained at a temperature in the range of 5-60° C.;
neutralizing the partially deacetylated chitin;
removing undissolved particles through sequential filtering steps;
adjusting the solution to a pH above 8, and raising the temperature of the solution to above 30° C.;
precipitating the fully dissolved and purified partially deacetylated chitin; and
recovering and washing said precipitate at a temperature above 50° C.

2. The composition according to claim 1, wherein the biomaterial composition further comprises at least one component selected from the group consisting of hydroxyapatite, calcium sulphate, sodium tripolyphosphate, alginate, collagen and hyaluronic acid.

3. A composition according to claim 1, wherein said solid component comprises said partially deacetylated chitin and calcium phosphates, and said liquid component comprises phosphoric acid.

4. A composition according to claim 1, comprising about 5 wt % of said partially deacetylated chitin.

* * * * *